(12) United States Patent
Harris et al.

(10) Patent No.: US 12,089,825 B2
(45) Date of Patent: Sep. 17, 2024

(54) DEVICES AND METHODS WITH EXPANDABLE BRUSH FOR CERVICAL AND ANAL SELF-COLLECTING SPECIMENS

(71) Applicants: Brent Harris, Carrollton, GA (US);
Anna Harris, Carrollton, GA (US)

(72) Inventors: Brent Harris, Carrollton, GA (US);
Anna Harris, Carrollton, GA (US)

(*) Notice: Subject to any disclaimer, the term of this patent is extended or adjusted under 35 U.S.C. 154(b) by 0 days.

(21) Appl. No.: 18/215,118

(22) Filed: Jun. 27, 2023

(65) Prior Publication Data
US 2023/0414207 A1 Dec. 28, 2023

Related U.S. Application Data

(60) Provisional application No. 63/431,662, filed on Dec. 9, 2022, provisional application No. 63/356,479, filed on Jun. 28, 2022.

(51) Int. Cl.
*A61B 10/02* (2006.01)
*A61B 10/06* (2006.01)

(52) U.S. Cl.
CPC .......... *A61B 10/0291* (2013.01); *A61B 10/06* (2013.01); *A61B 2010/0216* (2013.01)

(58) Field of Classification Search
None
See application file for complete search history.

(56) References Cited

U.S. PATENT DOCUMENTS

| | | | | |
|---|---|---|---|---|
| 3,776,219 | A * | 12/1973 | Brown | A61B 10/0291 600/572 |
| 5,092,345 | A * | 3/1992 | Sakita | A61B 10/0291 600/570 |
| 9,144,420 | B2 * | 9/2015 | Zavala | A61B 10/0291 |
| 2002/0068881 | A1 * | 6/2002 | Kobren | A61B 10/0291 600/569 |
| 2004/0116827 | A1 * | 6/2004 | Tiberio | A61B 10/0291 600/569 |
| 2005/0277847 | A1 * | 12/2005 | Belinson | A61B 10/0291 600/569 |
| 2008/0188769 | A1 * | 8/2008 | Lu | A61B 10/02 600/569 |

(Continued)

OTHER PUBLICATIONS

Written Opinion of the International Searching Authority, PCT/US2023/026379, Oct. 2, 2023.
International Search Report, PCT/US2023/026379.

*Primary Examiner* — Benjamin S Melhus
(74) *Attorney, Agent, or Firm* — RADLO & SU

(57) ABSTRACT

Embodiments of the present invention are directed to a portable insertion medical device (also referred to as "self-collection insertion plunger device" or "self-collection delivery plunger device") with the design of a brush body for self-collection of a plurality of specimens from female genitalia. In one embodiment, the self-collection insertion plunger device includes a brush portion having a plurality of bristles that expand outward with a tensile strength to collect a plurality of specimens after insertion for a predetermined amount of time. In another embodiment, the self-collection insertion plunger device has a brush body with a plurality of petals and a plurality of bristles for a wider coverage in the collection of a plurality of specimens, particularly as the plurality of petals expand after insertion into female genitalia.

26 Claims, 22 Drawing Sheets

(56) References Cited

U.S. PATENT DOCUMENTS

| | | | |
|---|---|---|---|
| 2009/0062690 A1* | 3/2009 | Kim | A61B 10/0291 600/573 |
| 2009/0062691 A1* | 3/2009 | Kim | A61B 10/0291 600/573 |
| 2009/0275859 A1* | 11/2009 | Kim | A61B 10/0291 600/569 |
| 2010/0305472 A1* | 12/2010 | Larkin | A61B 10/02 600/570 |
| 2013/0172778 A1* | 7/2013 | Teschendorf | A61B 10/0291 600/562 |
| 2015/0005665 A1* | 1/2015 | Weldon | A61B 1/00131 600/562 |
| 2016/0262734 A1* | 9/2016 | Chin-Ly | A61B 10/06 |
| 2016/0317132 A1 | 11/2016 | Markowitz et al. | |
| 2016/0331357 A1* | 11/2016 | Czarnecki | A61B 10/0291 |
| 2017/0112477 A1* | 4/2017 | Benning | A61B 10/02 |
| 2017/0303903 A1* | 10/2017 | de Koning | A61B 1/00103 |
| 2018/0078242 A1* | 3/2018 | Aghdam | A61B 5/4337 |
| 2018/0161020 A1* | 6/2018 | Friedlander | A61B 10/02 |
| 2018/0344300 A1* | 12/2018 | Burrows | A61B 10/0291 |
| 2020/0305851 A1* | 10/2020 | Gilbert | A61B 10/0291 |
| 2020/0360055 A1* | 11/2020 | Hong | A61L 15/28 |

* cited by examiner

INSERTION/DELIVERY
PLUNGER DEVICE 10 (self-collecting) insertion/delivery plunger device

AT LAB, SAMPLE WILL UNDERGO
LIQUID/CELLULAR ANALYSIS

NAAT / PCR (40-1)
- MOLECULAR ANALYSIS DETECTS CANCER AND PRE-CANCER CHANGES
- STD's
- HPV TYPES (CANCER RISKS)
  VAGINAL, UTERINE, CERVICAL

CULTURE (40-2)
GROW OUT & IDENTIFY VARIOUS INFECTIONS

LIQUID CYTOLOGY (40-3)
FOR PRE-CANCER/CANCER ANALYSIS BY PATHOLOGIST

INSERTION/DELIVERY
PLUNGER DEVICE 50 (self-collecting) insertion/delivery plunger device Petal Enlargement

DEVICES AND METHODS WITH EXPANDABLE BRUSH FOR CERVICAL AND ANAL SELF-COLLECTING SPECIMENS

CROSS REFERENCE TO RELATED APPLICATIONS

This application claims priority to U.S. Provisional Application Ser. No. 63/356,479 entitled "Cervical Self-Collecting Specimens Device with Expandable Brush," filed on 28 Jun. 2022, and U.S. Provisional Application Ser. No. 63/431,662 entitled "Cervical Self-Collecting Specimens Device with Expandable Brush," filed on 9 Dec. 2022, the disclosures of which are incorporated herein by reference in their entireties.

TECHNICAL FIELD

The present invention relates generally to medical devices, and more particularly portable medical device to obtain one or more specimens for screening of cervical cancer and other diseases.

SUMMARY OF THE DISCLOSURE

Embodiments of the present invention are directed to a portable insertion medical device (also referred to as "self-collection insertion plunger device" or "self-collection delivery plunger device") with the design of a brush body for self-collection of a plurality of specimens from a female genitalia. In a first embodiment, the self-collection insertion plunger device includes a brush portion having a plurality of bristles that expand outward with a tensile strength to collect a plurality of specimens after insertion for a predetermined amount of time. A first type of the self-collection insertion plunger device is designed for placement into female genitalia to collect vaginal specimens for subsequent testing for uterus cancer screening, cervical cancer screening, or vaginal cancer screening, or any combination of multiple tests. In a second embodiment, a second type of the insertion plunger device is designed for insertion into a person's anus for collecting samples for colon cancer and/or rectal cancer screening. In a third embodiment, the self-collection insertion plunger device has a brush body with a plurality of petals and a plurality of bristles for a wider coverage in the collection of a plurality of specimens, particularly as the plurality of petals expand after insertion into a female genitalia.

Broadly stated, a specimen collection device comprises a generally cylindrical tubing casing; and a brush body placed into the tubing casing, the brush body comprising a plurality of bristles on a first end and a string attached on a second end; wherein the specimen collection device functions between a first state and a second state, the plurality of bristles on the brush body remaining in an unexpanded form during the first state, the plurality of bristles on the brush body expanding outward in an expanded form during the second state, and, during the second state, the plurality of bristles collects specimens from an orifice of a patient when inserted into the orifice for a predetermined amount of time.

In one embodiment, a specimen collection device comprises an outer tubular member; and an inner tubular member inserted through the outer tubular member; a single-unit brush body comprising a plurality of petals and a plurality of bristles, the single-unit brush body attached to a string, the string of the brush body inserted through the inner tubular member; wherein the specimen collection device functions between a first state and a second state, the plurality of petals and the plurality of bristles on the brush body remaining in an unexpanded form during the first state, the plurality of petals and the plurality of bristles on the brush body expanding outward in an expanded form during the second state, and during the second state, the plurality of petals and the plurality of bristles collect a plurality of specimens from an orifice of a patient when inserted into the orifice for a predetermined amount of time.

In another embodiment, a specimen self-collection device comprises an outer tubular member; and an inner tubular member inserted through the outer tubular member; a brush body with a string, the string of the brush body inserted through the inner tubular member, the brush body comprising a plurality of specimen collection elements; wherein the specimen self-collection device functions in a first state and a second state, the plurality of specimen collection elements on the brush body remaining in an unexpanded form during the first state, the plurality of specimen collection elements on the brush body expanding outward in an expanded form during the second state, and, during the second state, the plurality of specimen collection elements collects specimens when inserted into an orifice for a predetermined amount of time.

In some embodiments, the orifice comprises a vaginal orifice. In other embodiments, the orifice comprises an anal orifice.

In some embodiments, the plurality of bristles on the brush body comprise medical-grade silicone.

In some embodiments, the plurality of bristles on the brush body comprise medical-grade silicone rubber.

In some embodiments, the plurality of bristles on the brush body comprise a tensile strength that is selected for matching with an anatomical parameter of the orifice.

In some embodiments, the plurality of bristles on the brush body comprise a size dimension that is suitable for a population community in a geographical area.

In some embodiments, the plurality of bristles on the brush body comprise a size dimension that is suitable for a plurality of females.

In some embodiments, the plurality of bristles on the brush body comprise a tensile strength that is selected for matching with an anatomical parameter of the vaginal orifice.

In some embodiments, the plurality of bristles on the brush body comprise a tensile strength that is selected for matching with an anatomical parameter of the anal orifice.

The structures and methods of the present invention are disclosed in the detailed description below. This summary does not purport to define or limit the invention in any way. The invention is defined by the claims. These and other embodiments, features, aspects, and advantages of the invention will become better understood with regard to the following description, appended claims, and accompanying drawings.

BRIEF DESCRIPTION OF THE DRAWINGS

The invention will be described with respect to specific embodiments thereof, and reference will be made to the drawings, in which.

DETAILED DESCRIPTION

Figure 1:
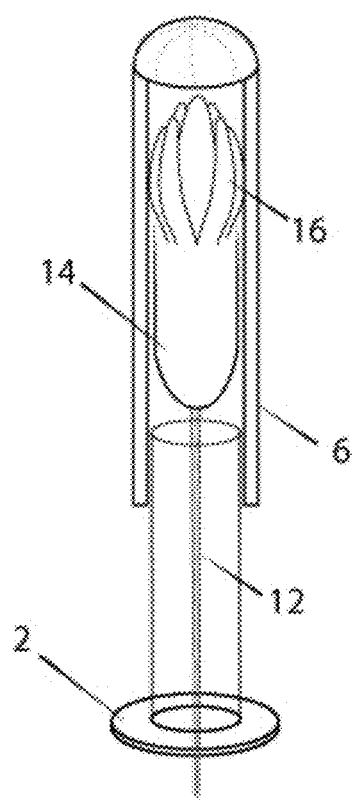
FIG. 1 is a diagram illustrating a first embodiment of an insertion plunger device with an expandable brush in a first position in accordance with the present invention.

A description of structural embodiments and methods of the present invention is provided with reference to FIGS. 1-34. It is to be understood that there is no intention to limit the invention to the specifically disclosed embodiments but that the invention may be operated using other features, elements, methods, and embodiments that are known to those of skill in the art. Like elements in various embodiments are commonly referred to with like reference numerals.

FIG. 1 is a diagram illustrating a first embodiment of an insertion plunger device 10 (also referred to as "delivery plunger device) with an expandable brush 12 (also referred to as "VAGIGUARD"™) in the first position. The expandable brush 12 includes a brush body 14, a brush portion 16 on a first end that is expandable upon insertion into female genitalia (also referred to as "vaginal orifice"), and a string 18 on a second end attached to the brush body 14 of the expandable brush 12. In one embodiment, the brush portion 16 of the expandable brush 12 has a plurality of bristles that extend outward in a rounded shape or a rounded fashion. A suitable material for implementing the brush portion 16 includes silicone, or other types of materials with a similar tensile strength. The insertion plunger device 10 has three case components: a circular tap 2, a cylindrical tubing 4, and an external wall section 6. The string 18 is attached to the expandable brush 12 on one end and the circular tap 2 on the other end. The cylindrical tubing 4 is partially inserted within the external wall section 6 on the one end and attached to the circular tap 2 on the other end. The string 18 is placed inside the cylindrical tubing 4.

The brush portion 16 of the expandable brush 12 of the insertion plunger device 10 has two states (or two positions), a first state (also referred to as the "original state") in which the brush portion 16 is not expanded and a second state (also referred to as the "expanded state") in which the brush portion 16 is expanded outward. As shown in FIG. 1, the brush portion 16 of the expandable brush 12 of the insertion plunger device 10 is in the first state or the original state, where the brush portion 16 is not expanded.

Figure 2:
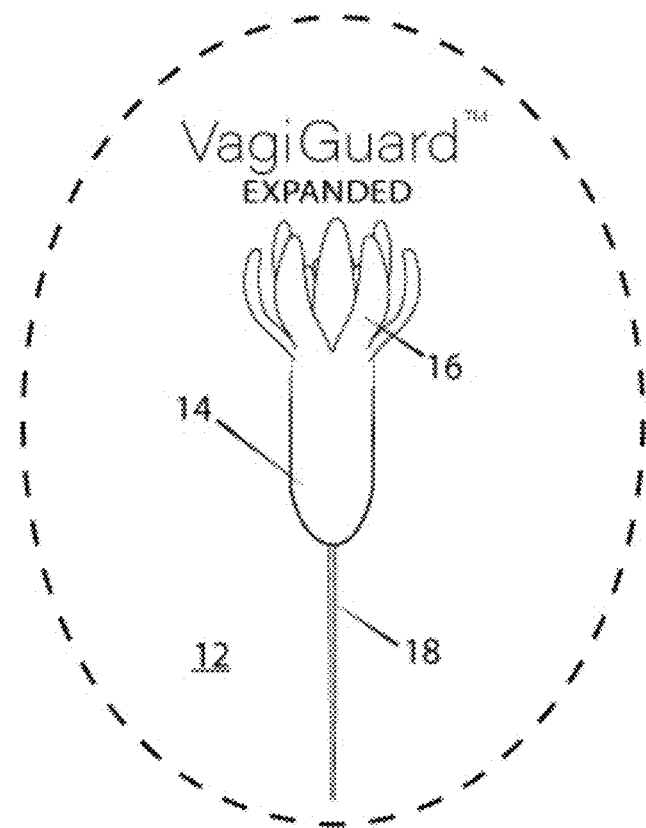
FIG. 2 is a diagram illustrating the expandable brush that has the brush body and the brush portion of the insertion plunger device in a second position of the first embodiment in accordance with the present invention.
Figure 3:
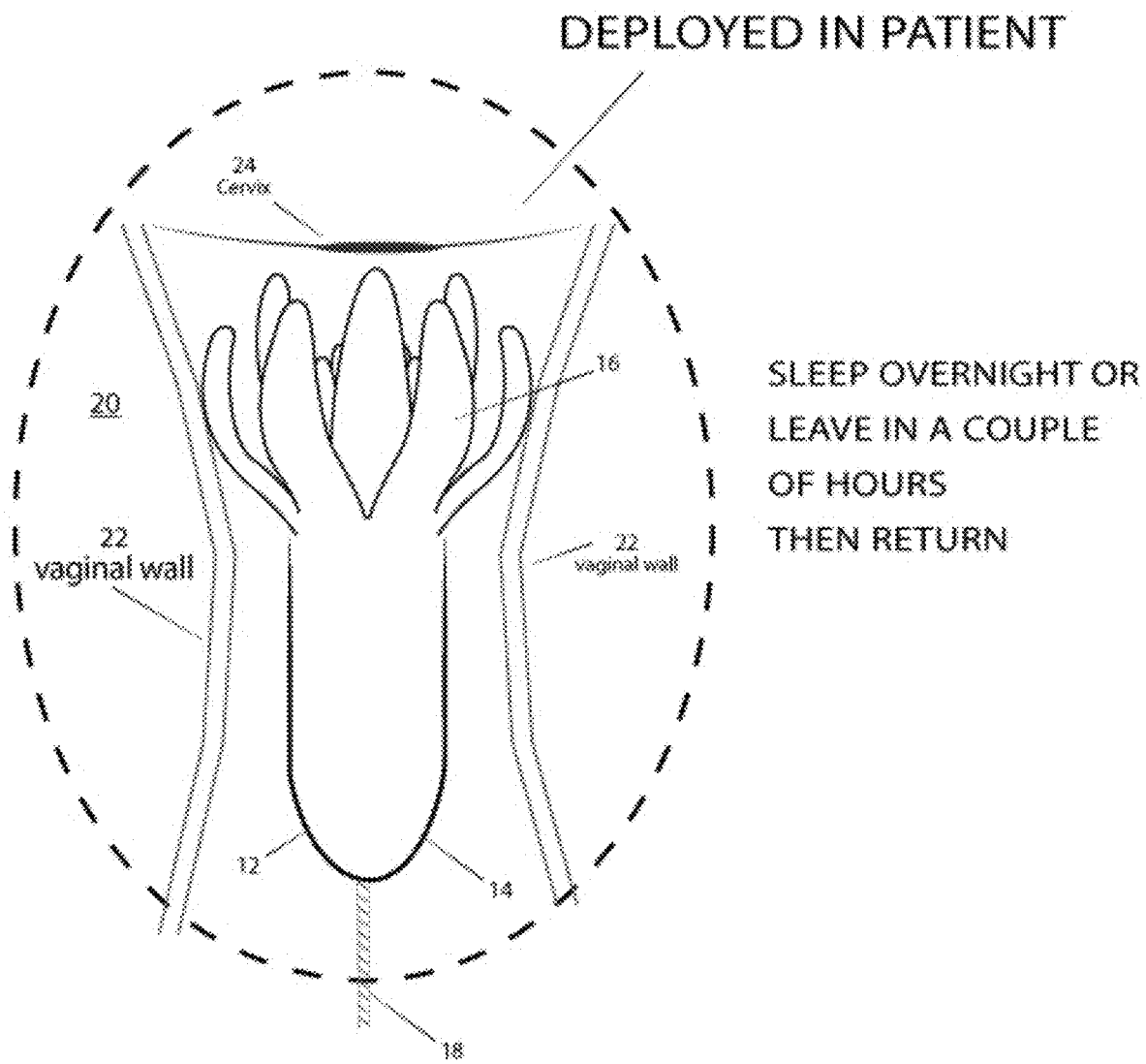
FIG. 3 is a diagram illustrating the deployment of the insertion plunger device into the cervix of female genitalia with the expandable brush in accordance with the present invention.

FIG. 2 is a diagram illustrating the expandable brush 12 that has the brush body 14 and the brush portion 16 of the insertion plunger device 10 in the second position of the first embodiment. The brush portion 16 of the expandable brush 12 of the insertion plunger device 10 is in the second state or the expanded state, as shown in FIG. 2, where the brush portion 14 is expanded outward. The brush portion 16 comprises a plurality of bristles that expand outward to capture specimens or samples while inserted into female gentalia as shown in FIG. 3. In some embodiment, a plurality of specimens refer to following: Cytology, Pathology, Cellular, Bacterial, Viral, Genetic, and other Biomarker(s) specimen material. The plurality of specimens may also include bacteria, a virus, deoxyribonucleic acid (DNA), ribonucleic acid (RNA), cervical cells, endometrial cells, vaginal cells, and other applicable cells.

Figure 25:
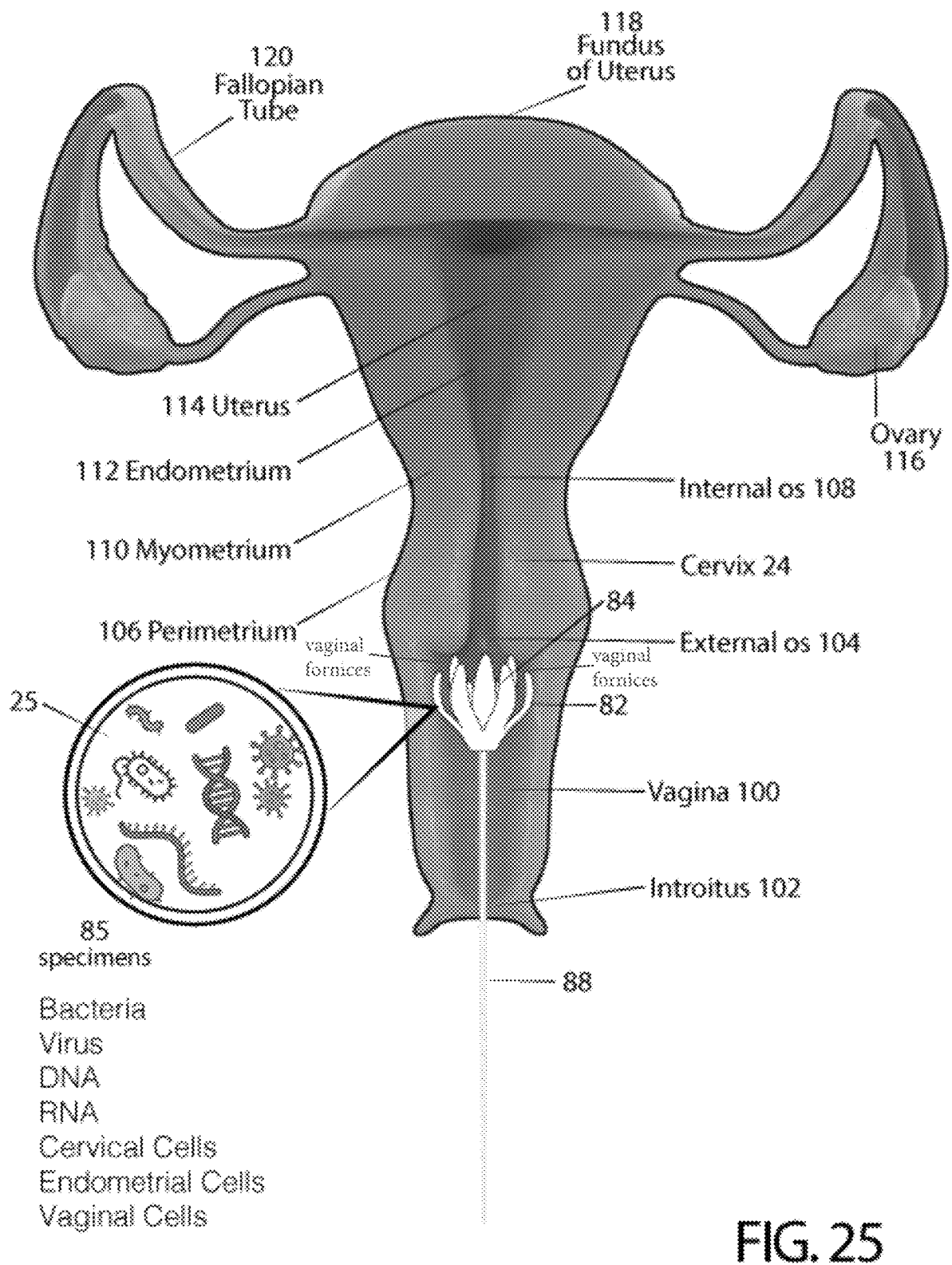
FIG. 25 is a pictorial diagram illustrating a partial female anatomy with the insertion of the self-collecting insertion/delivery plunger device in accordance with the present invention.

FIG. 3 is a diagram illustrating the deployment of the insertion plunger device 10 into a cervix 24 of female genitalia 20 with the expandable brush 12. An individual can deploy the insertion plunger device 10 by herself for self-collected specimens. Alternatively, a medical worker, such as a doctor or a nurse, can deploy the insertion plunger device 10 into a patient for collecting one or more (or multiple) specimens. As for the methodology, the medical worker inserts (or deploys, or places) the insertion plunger device 10 into a vaginal wall 22 until the brush portion 16 extends toward (or touches in one embodiment) the cervix 24 of the female genitalia 20. The brush portion 16 of the expandable brush 14 then expands outward against the vaginal wall 22 and the cervix 24 (referred to as being in the second position or the expanded state of the expandable brush 14). When the insertion plunger device 10 is inserted into the female genitalia 20 as illustrated in FIG. 3, the first end faces the cervix 24 and the second end faces an introitus of the female genitalia 20, such as an introitus 102 as illustrated in FIG. 25. In one embodiment, when the insertion plunger device 10 is inserted into the female genitalia 20, the brush portion 16 expands outwards such that the insertion plunger device 10 becomes a conical shape where the first end is wider than the second end and is tapered, thereby allowing the insertion plunger device to naturally be retained within the vaginal orifice and preventing the insertion plunger device 10 from withdrawing from the female genitalia 20 without an intervention by the individual or the patient (e.g., does not withdraw due to gravity, body movement by the individual or the patient, movement from vaginal wall and/or the cervix, and/or the like). In one example, the brush portion 16 expands to a size that prevents the insertion plunger device 10 from advancing past an external os associated with the cervix 24.

The individual or the patient keeps the expandable brush 14 in the female genitalia 20 for a predetermined amount of time, for example, two hours or an amount of time corresponding to overnight. Sleep overnight provides sufficient time for the brush portion 16 that has been expanded to collect one or more specimens (or multiple specimens) from the interior of the vaginal wall 22 and around the cervix 24. In one embodiment, the predetermined amount of time depends on the purpose of a medical condition test that the insertion plunger device 10 is being used. As an example, when performing a sexually transmitted disease (STD) test, the predetermined amount of time may be a few minutes, for example, five minutes. As another example, when performing a cervical cancer test, the predetermined amount of time may be a few hours, such as two or more hours.

After the predetermined amount of time has been met, the medical worker (or the patient herself, or the individual herself) removes the insertion plunger device 10 from the female genitalia 20 of the patient (or individual). The self-collected specimens (or specimens collected by a medical worker) is placed in a container for sending to a laboratory for application of the specimens for testing of various symptoms, including sexually transmitted disease (STDs), endometrial cancer screening/uterus cancer screening, cervical cancer screening, or vaginal cancer screening, or any combination of multiple tests.

Figure 4:
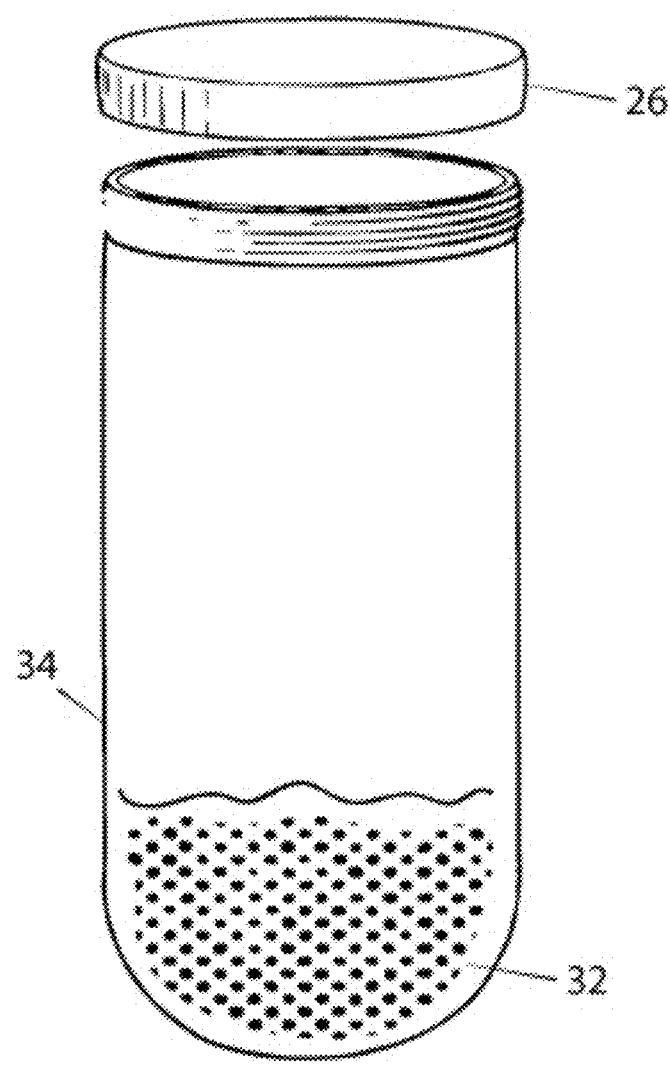
FIG. 4 is a diagram illustrating one embodiment of a return vessel with preservative liquid in accordance with the present invention.

FIG. 4 is a diagram illustrating one embodiment of a return vessel 30 (also referred to as "container" or "jar") with preservative liquid 32 (also referred to as "return liquid"). The return vessel 30 including a vessel body 34 and a vessel cap 36. A predetermined amount of preservative (or "return liquid") 32 is poured into the vessel body for preserving the integrity of the specimens. The vessel cap 36 matches with the vessel body 34 to enclose the return vessel 30.

Figure 5:
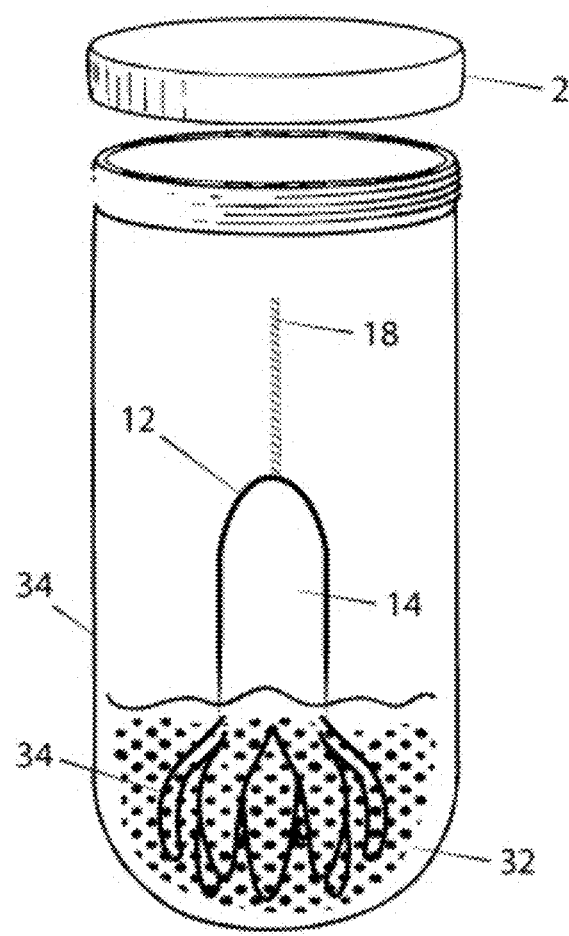
FIG. 5 is a pictorial diagram illustrating one embodiment of the process steps in placing the insertion plunger device in a return container with a cap for sending to a laboratory in accordance with the present invention.

FIG. 5 is a pictorial diagram illustrating a plurality of steps used in placing the VAGIGUARD™ device in the return container with a cap for sending to a laboratory. At step 30-1, after the insertion plunger device 10 has been expanded to collect or absorb specimens from the female genitalia 20, the insertion plunger device (or VAGIGUARD™) 10 is placed in the return vessel 30 such that the brush portion 16 of the insertion plunger device 10 is soaked in the preservative liquid 32 to maintain moisture and preserve the integrity of the specimens. At step 30-2, the cap is placed over the vessel body 34 to enclose the return vessel 30 without leakage. At step 30-3, a medical worker or an individual puts the return vessel 30 into a box for shipping. At step 30-4, the box including the return vessel 30 is mailed to a laboratory for testing the existence or absence for detecting or screening multiple diseases or cancers from the single collected specimens, or a particular disease or a particular cancer.

Figure 6:
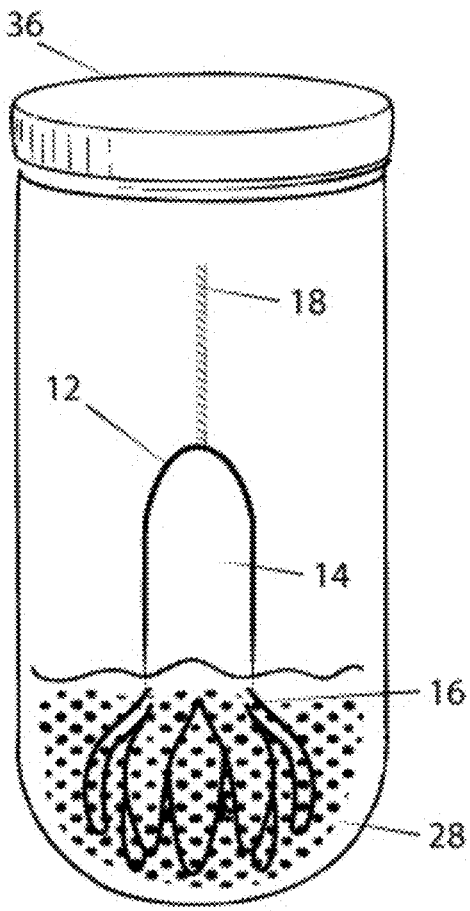
FIG. 6 is a pictorial diagram illustrating one embodiment of the process steps for the laboratory to analyze the specimens with liquid/cellular analysis in accordance with the present invention.

FIG. 6 is a pictorial diagram illustrating a plurality of exemplary steps for the laboratory to analyze the specimens (or "samples") with liquid analysis (or "cellular analysis"). At step 40-1, a medical worker at the laboratory conducts molecular analysis on the collected specimens ("vaginal specimens") from the cervix, e.g., subjecting the one or more specimens to nucleic acid amplification test (NAAT) and/or a real-time polymerase chain reaction (PCR) test, or any other test(s) for detecting cancer and/or pre-cancer changes, STDs, and/or human papillomavirus (HPV) types (on cancer risks). At step 40-2, the vaginal specimens undergo culture testing by growing out and identify various infections. At step 40-3, the medical worker then treats the vaginal specimens or the preservative liquid in liquid cytology for pre-cancer or cancer analysis by a pathologist.

Figure 7:
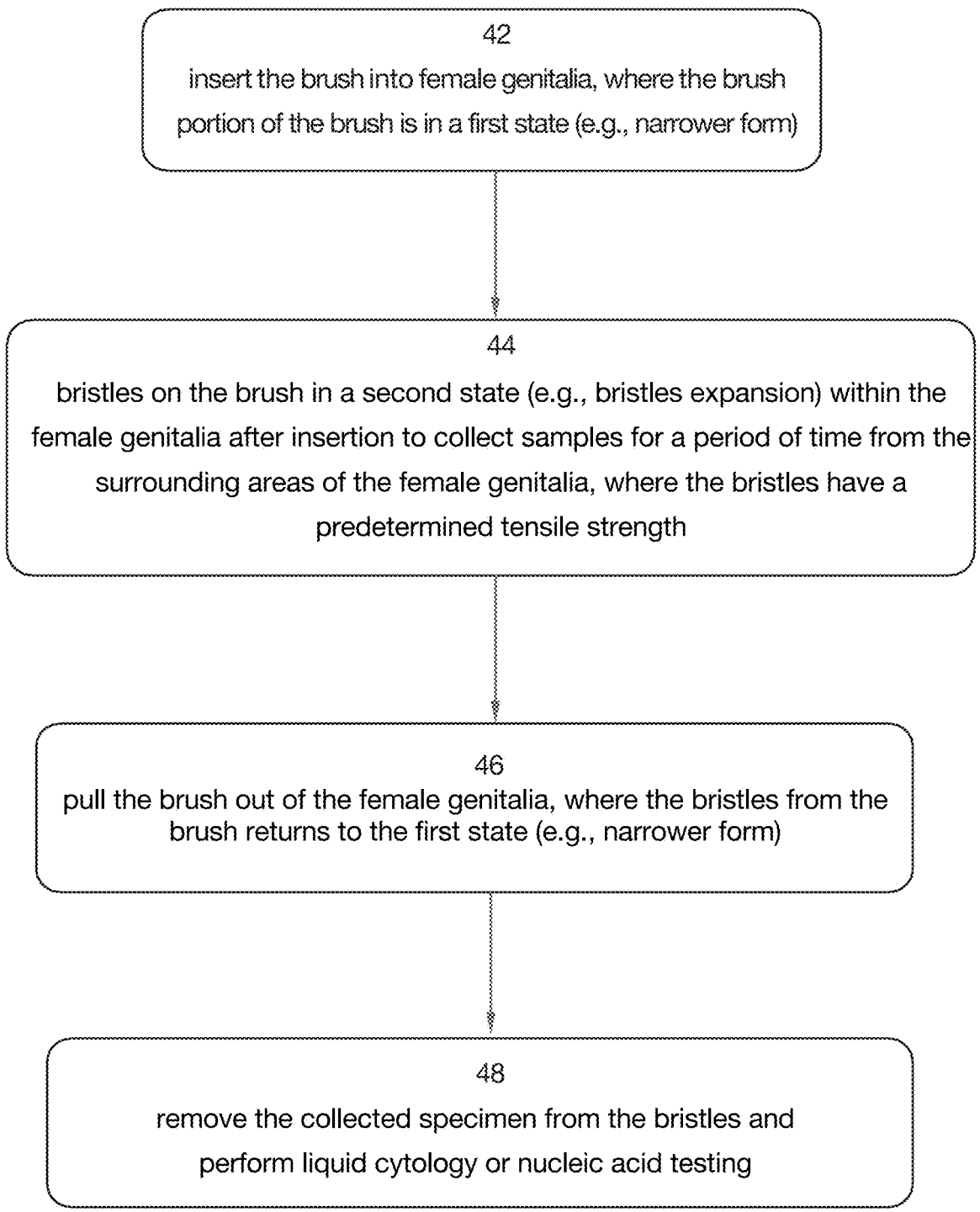
FIG. 7 is a flow diagram illustrating one embodiment of the process steps in deploying the insertion plunger device into the cervix of female genitalia with the expandable brush to collect specimens in accordance with the present invention.

FIG. 7 is a flow diagram illustrating the process 41 of inserting the insertion plunger device into the cervix of female genitalia with the expandable brush to collect specimens. At step 42, the brush portion 12 of the insertion plunger device 10 initially is in its first position or its first state (e.g., narrower form). At step 44, a medical worker or other individual inserts the insertion plunger device 10 into the female genitalia 20. At such time the brush portion 16 in the insertion plunger device 10 expands into the second position (or the second state) within the female genitalia 20 to collect specimens (e.g., vaginal specimens and/or samples) from the surrounding areas of the female genitalia 20 for at least a predetermined period of time. In some embodiments, the brush portion 16 has soft bristles that expand upon insertion into the female genitalia 20 with a predetermined tensile strength. In other embodiments, upon insertion into the female genitalia 20, the brush portion 16 has soft bristles that expand at a tensile strength dependent on one or more anatomical parameters of the female genitalia 20 of a particular female. In an embodiment, the tensile strength of the brush portion 16 is an amount that withstands a compressive force of one or more muscles of the female genitalia (e.g., the vagina and/or the cervix and the compressive force does not cause the brush portion 16 to disassemble), but does not harm the female genitalia (e.g., cause bleeding, laceration, and/or other tissue damage). The tensile strength of the brush portion 16 is selected and customized depending on the one or more anatomical parameters of the female genitalia 20 of the particular female. In further embodiments, the brush portion 16 of the insertion plunger device 10 has soft bristles that can be designed and manufactured with a wide variety of tensile strengths, or a combination of multiple tensile strengths, such that medical personnel can select a particular insertion plunger device 10 to best match with the particular anatomy of the female genitalia 20 in the woman, depending on the variables of the female anatomy determined through prior diagnosis, or through a computer simulation of the female anatomy in matching (or customizing) with the variations (or variables) brush portion 16 of the insertion plunger device 10. At step 46, the medical personnel pulls the insertion plunger device 10 out of the female genitalia 20, wherein the brush portion 16 returns to the first state (e.g., narrower form), and then places the insertion plunger device 10 into the return vessel 30. At step 48, the medical worker removes the collected vaginal specimens from the return vessel 30 and performs liquid cytology or nucleic acid testing for cancer screening, or other tests to discern the existence or absence of one or more diseases.

Figure 8:
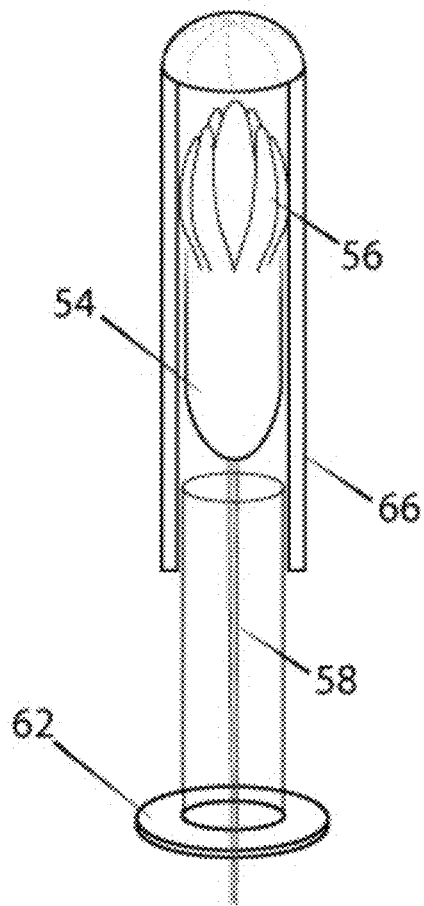
FIG. 8 is a diagram illustrating a second embodiment of an insertion plunger device with an expandable brush for an anal application in a first position of the second embodiment in accordance with the present invention.

FIG. 8 is a diagram illustrating a second embodiment of an insertion plunger device 50 (also referred to as "delivery plunger device) with an expandable brush (also referred to as "ANALGUARD"™). The expandable brush 52 includes a brush body 54, a brush portion 56 on a first end that is expandable upon insertion into a person's anus (also referred to as "anal orifice") for rectal examination and a string 58 on a second end attached to the brush body 54 of the expandable brush 52. The insertion plunger device 50 has three case components: a circular tap 62, a cylindrical tubing 64, and an external wall section 66. The string 58 is attached to the expandable brush 12 on one end and the circular tap 62 on the other end. The cylindrical tubing 64 is partially inserted within the external wall section 66 on the one end and attached to the circular tap 2 on the other end. The string 58 is placed inside the cylindrical tubing 64.

The brush portion 56 of the expandable brush 52 of the insertion plunger device 50 has two states, a first state in which the brush portion 56 is not expanded and a second state in which the brush portion 56 is expanded outward. As shown in FIG. 8, the brush portion 56 of the expandable brush 52 of the insertion plunger device 50 is in the first state, where the brush portion 56 is not expanded. Similarly to the brush portion 16, the tensile portion of the brush portion 56 is at an amount that withstands a compressive force of one or more muscles of the anus (e.g., the compressive force does not cause the brush portion 16 to disassemble), but does not harm the anus (e.g., cause bleeding, laceration, and/or other tissue damage).

Figure 9:
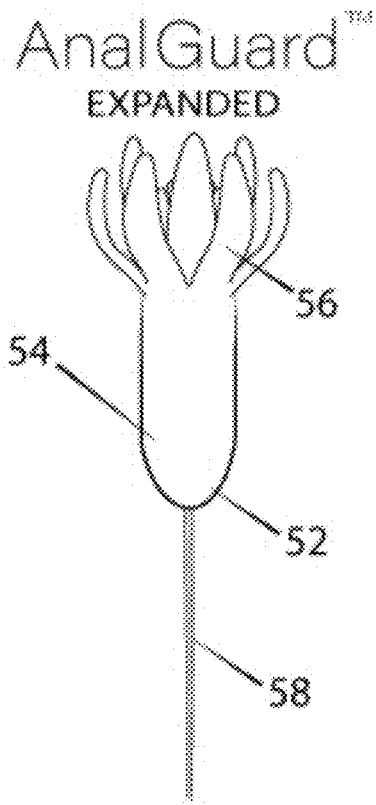
FIG. 9 is a diagram illustrating the expandable brush that has the brush body and the brush portion of the insertion plunger device for an anal application in a second position of the second embodiment in accordance with the present invention.

FIG. 9 is a diagram illustrating the second embodiment of the insertion plunger device 50 with the expandable brush 52 that has the brush body 54 and the brush portion 56. The brush portion 56 of the expandable brush 52 of the insertion plunger device 50 is in the second state, as shown in FIG. 2, where the brush portion 56 is expanded outward.

Figure 10:
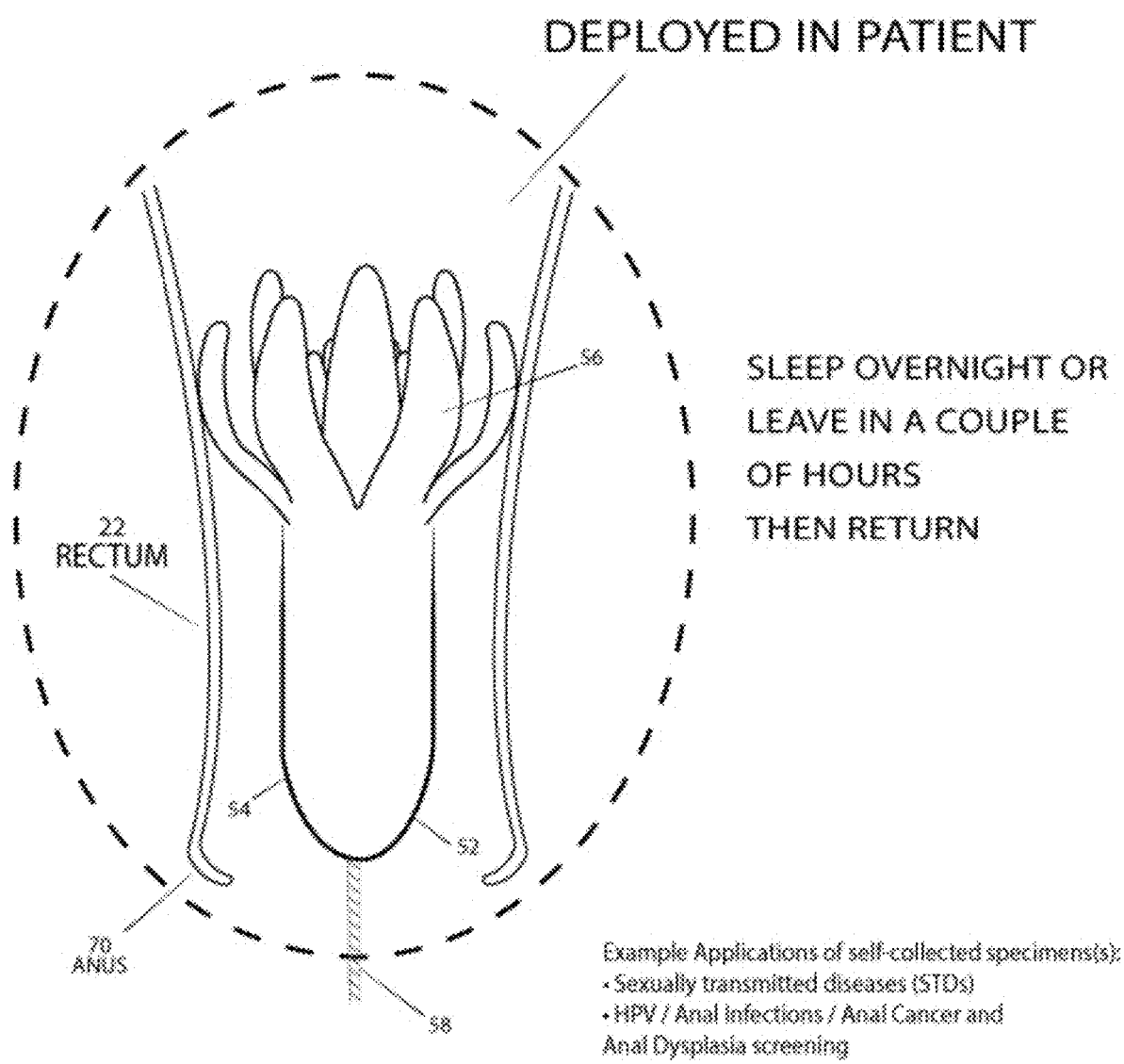
FIG. 10 is a diagram illustrating the deployment of the insertion plunger device into the anus and the rectum with the expandable brush in accordance with the present invention.

FIG. 10 is a diagram illustrating the deployment of the insertion plunger device 50 into an anus 70 and a rectum 22 with the expandable brush 56. An individual can deploy the insertion plunger device 50 by himself or herself for self-collected specimens. Alternatively, a medical worker, such as a doctor or a nurse, can deploy the insertion plunger device 50 into a patient for collecting one or more (or multiple) specimens. When the insertion plunger device 50 is inserted into the anus 70 and the rectum 72 as illustrated in FIG. 10, the first end faces away from the anus 70 and the second end faces towards the anus 70. In one embodiment, when the insertion plunger device 50 is inserted into the anus 70 and the rectum 72, the brush portion 56 expands outwards such that the insertion plunger device 50 becomes a conical shape where the first end is wider than the second end and is tapered, thereby allowing the insertion plunger device to naturally be retained within the rectum 72 and preventing the insertion plunger device 50 from withdrawing from the rectum 72 without an intervention by the individual or the patient (e.g., does not withdraw due to gravity, body movement by the individual or the patient, movement from anus 70 and/or the rectum 72, and/or the like).

As for the methodology, the medical worker inserts (or deploys, or places) the insertion plunger device 50 into the anus 70 and the rectum 72 until the brush portion 56 extends in the area or wall of the rectum 72. The brush portion 56 of the expandable brush 54 then expands outward against the wall of the rectum 72 (referred to as being in the second position or the expanded state of the expandable brush 54). The individual or the patient keeps the expandable brush 54 in the rectum 72 for a predetermined amount of time, for example, two hours or an amount of time corresponding to overnight. Overnight sleep provides sufficient time for the brush portion 56 that has been expanded to collect one or more specimens (or multiple specimens) from the interior of the wall of the rectum 72. Similar to those described in association with FIG. 3, in one embodiment, the amount of time depends on the purpose of a medical condition test that the insertion plunger device 50 is being used for.

After the predetermined amount of time has been met, the medical worker (or the patient himself or herself, or the individual himself or herself) removes the insertion plunger device 50 from the rectum 72 of the patient (or individual). The self-collected specimens (or specimens collected by a medical worker) are placed in a container for sending to a laboratory for application of the specimens for testing of various symptoms, including rectal cancer (cancer inside the rectum), colon cancer (also referred to as "colorectal cancer"—cancer inside the colon), anal cancer, rectal cancer screening, colon cancer screening, or anal cancer screening, or any combination of multiple tests. In addition, the self-collected specimens can be used for testing of various symptoms sexually transmitted diseases (STDs), and human papillomavirus (HPV)/anal infections/anal cancer and anal dysplasia screening.

Figure 11:
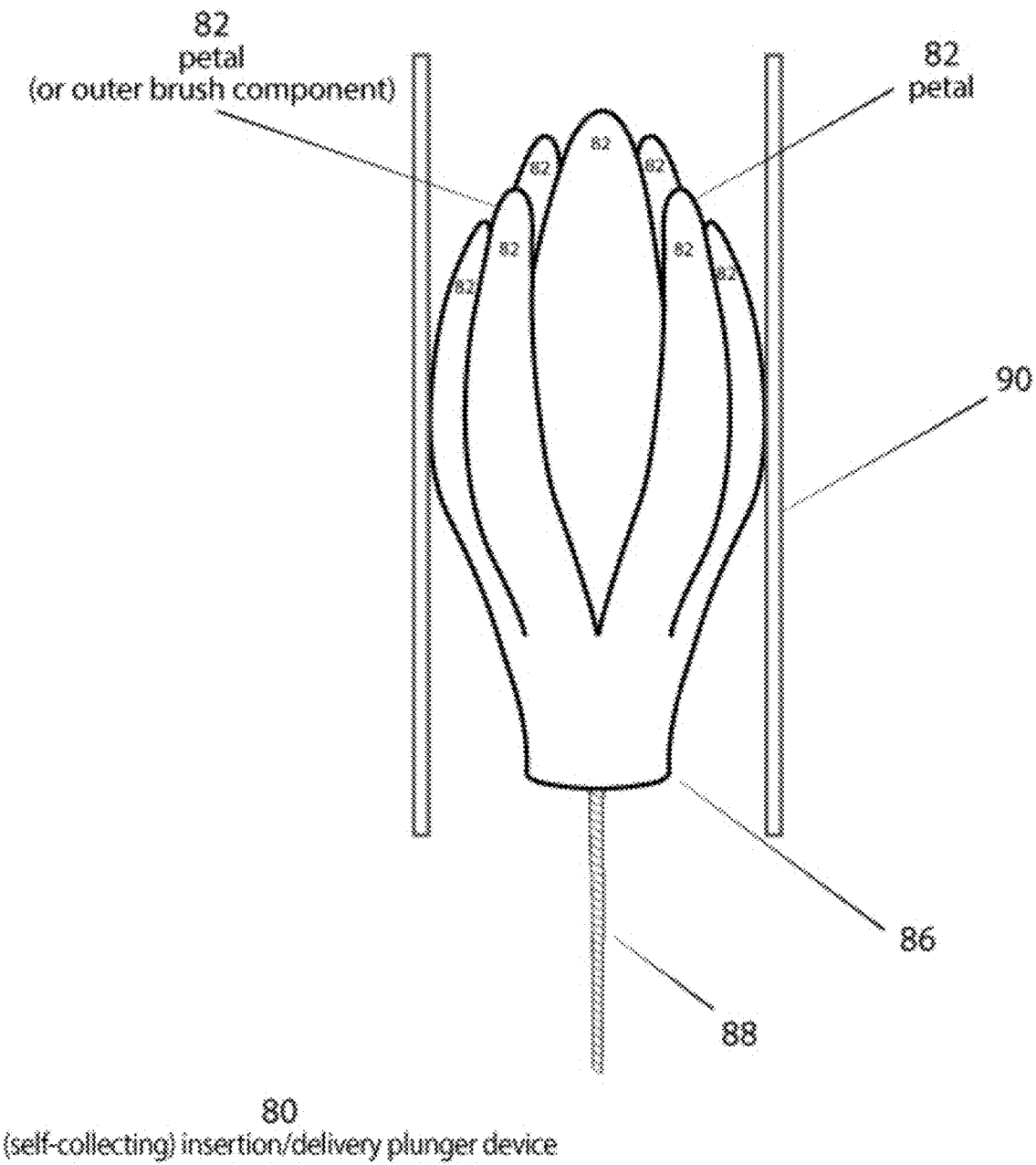
FIG. 11 is a diagram illustrating a third embodiment of a self-collecting insertion/delivery plunger device in a compression form before insertion in accordance with the present invention.
Figure 12:
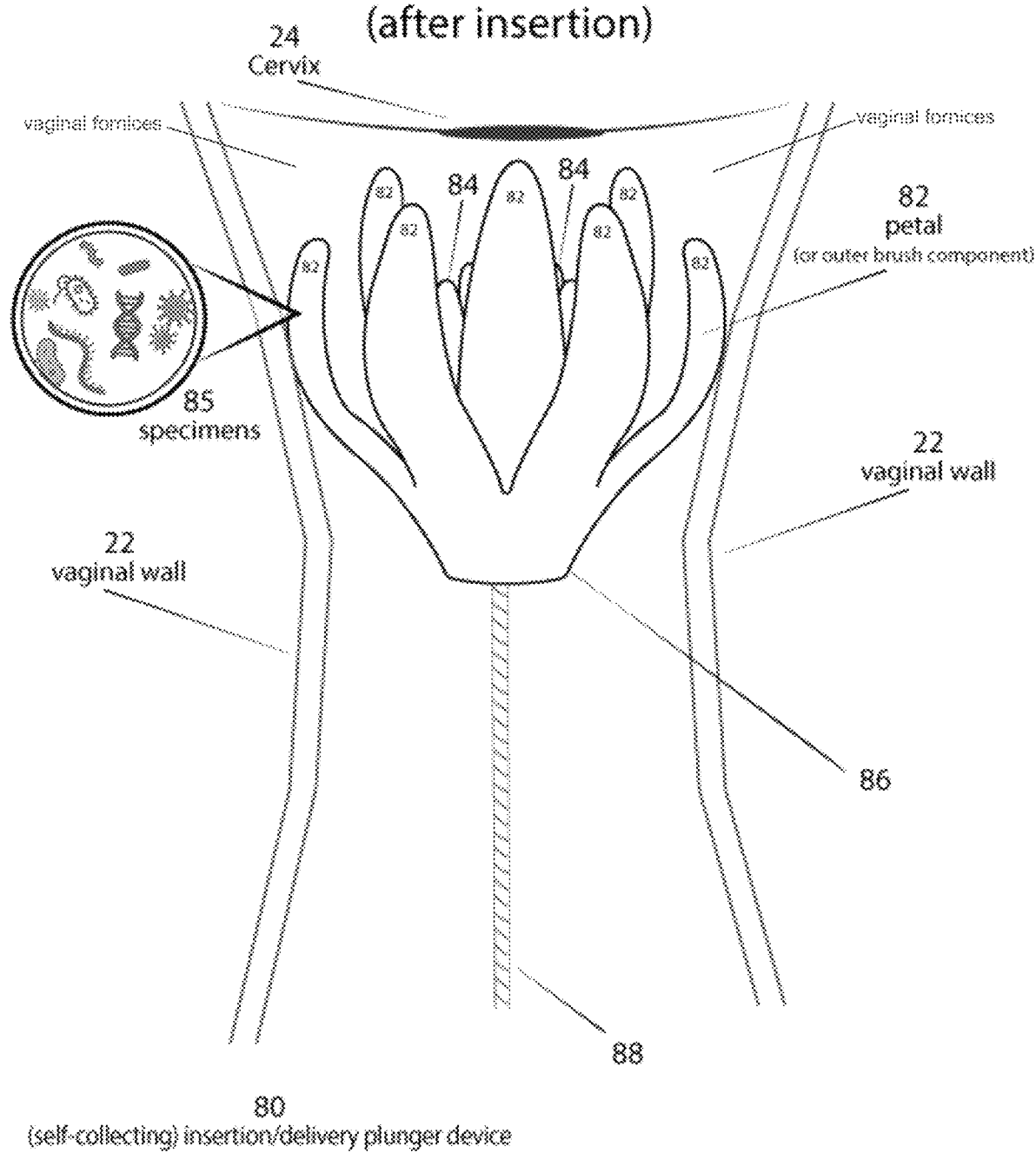
FIG. 12 is a diagram illustrating the third embodiment of the self-collecting insertion/delivery plunger device in an expanded form after insertion and during collection in accordance with the present invention.

FIG. 11 is a diagram illustrating a third embodiment of a self-collecting insertion/delivery plunger device 80 in a compression form (or "original form" or "original state") before insertion. In this embodiment, the self-collecting insertion plunger device 80 has an internal tubing 90 and includes a plurality of petals (also referred to as "leaves") 82 coupled to a base 86, which in turn coupled to a string 88. Within the plurality of petals 82, there are also a plurality of bristles 84 (as shown in FIG. 12), but bristles 84 may not be visible when the self-collecting insertion/delivery plunger device 80 is in its original state. The internal tubing 90 has an interior wall that holds the twelve petals 82. In one embodiment, the plurality of petals 82 includes twelve petals in the self-collecting insertion plunger device 80. One of ordinary skill in the art would recognize that a different number of petals, with greater even number such as fourteen, sixteen, and so, or with a lesser even number such as ten, eight, six and so on, as well as an odd number of petals, can be practiced within the spirit of the present invention. The self-collecting insertion/delivery plunger device 80 is packaged and sterilized before shipment for sale to users.

In one embodiment, the plurality of petals 82 and the plurality of bristles 84 in the self-collecting insertion/delivery plunger device 80 should self-locate themselves (e.g., adjusting a position and/or orientation) inside the cervix 24, such as in the middle of the cervix 24 or around the middle where the plurality of bristles 84 are located. In one embodiment, the self-collection insertion/delivery plunger device 80 self-locates by adjusting its position and/or orientation as the plurality of petals 82 and/or the plurality of bristles 84 expands such that the plurality of petals 82 and the plurality of bristles 84 adjust its position towards a wider section of the female genitalia 20 (e.g., toward the cervix 24 and away from an introitus 102 as illustrated on FIG. 25). However, the self-collecting insertion/delivery plunger device 80 may also able to collect a sufficient average specimens from a cellular standpoint or a microbiology standpoint, even though the plurality of petals 82 and the plurality of bristles 84 are not necessary ideally placed. In one embodiment, the sufficient average of specimens is based on a type of sample the specimens are and/or a type of analysis that the specimens are being subjected to. As a first example, when the specimens are microbiology samples, the sufficient average of specimens is an amount of specimens to visualize a condition being tested for on a microscope slide. As a second example, when the specimens are molecular samples, the sufficient average of specimens is an amount of specimens to accurately diagnose the condition using molecular analysis. As a third example, when the specimens are pathology samples, the sufficient average of specimens is an amount of specimens to perform a cytology analysis (e.g., a liquid based cytology analysis).

The design of the self-collecting insertion/delivery plunger device 80 in this embodiment includes a combination of the plurality of petals 82 and the plurality of bristles 84. In another embodiment, the self-collecting insertion/delivery plunger device 80 can also be designed with just the plurality of petals 82 without the plurality of bristles 84. In a further embodiment, the self-collecting insertion/delivery plunger device 80 can also be designed with just the plurality of bristles 84 without the plurality of petals 82.

FIG. 12 is a diagram illustrating the third embodiment of the self-collecting insertion/delivery plunger device 80 in an expanded form after insertion into a cervix 24 of female genitalia 20 with the expandable a plurality of petals 82 and a plurality of bristles (also referred to as "brushes") 84. An individual can deploy the insertion plunger device 80 by herself for self-collected specimens 85. Alternatively, a medical worker, such as a doctor or a nurse, can deploy the insertion plunger device 80 into a patient for collecting one or more (or multiple) specimens 85.

The plurality of petals 82, the plurality of bristles 84, and the base 86 are designed and manufactured as a single unit made of medical silicone rubber (also referred to as "medical grade silicone"), with the string 88 attached to the base 86 in the single unit. In another embodiment, the string 88 is designed and manufactured as a single unit as part of the plurality of petals 82, the plurality of bristles 84, and the base 86. Silicone can be classified as "medical grade" and safe to apply in medical applications after testing and obtaining an approval from the United States Food and Drug Administration (FDA or USFDA). In one example, there are several different types of commercially available silicones; however, the most commonly used for medical devices are High-Consistency Rubber (HCR) or Liquid Silicone Rubber (LSR) that involves the manufacture of solid silicone rubber into rolled sheets that are partially cured using peroxide catalyst additives. In another example, silicone rubber is an elastomer (rubber-like material) composed of silicone—itself a polymer—containing silicon together with carbon, hydrogen, and oxygen. Silicone rubbers are widely used in industry, and there are multiple formulations. Silicone rubbers are often one- or two-part polymers, and may contain fillers to improve properties or reduce cost. In a further example, silicone rubbers are man-made polymer materials that have a wide range of industrial and manufacturing applications. The various types of silicone rubbers include room temperature vulcanize, liquid silicone, fluorosilicone and high-consistency rubber. In one example, the plurality of petals 82, the plurality of bristles 84, and the base 86 is made of a different material that has passed the FDA's biocompatibility testing (e.g., passed FDA's sensitization, irrigation, cytotoxity, and heavy metal tests).

In some embodiments, the medical silicone rubber of the plurality of petals 82 and the plurality of bristles 84 are soft and pliable. The medical silicone rubber of the plurality of petals 82 and the plurality of brushes 84 has substantial (or significant) tensile strength to stretch or pull without breaking. In some embodiments, tensile strength of the plurality of petals 82 and the plurality of brushes 84 is sufficient to prevent tearing apart during insertion, extraction and/or laboratory processing. In other embodiments, the medical silicone rubber of the plurality of petals 82 and the plurality of brushes 84 have sufficient tensile strength to stretch or pull without breaking.

As for the methodology, an individual or a medical worker inserts (or deploys, or places) the insertion plunger device 80 into an area bounded by a vaginal wall 22 until the twelve petals 82 extend outward or toward (or touch) the cervix 24 of the female genitalia 20, and the plurality of bristles 24 extend outward or toward (or touches) the cervix 24 of the female genitalia 20. In this embodiment, the twelve petals 82 are organized to expand with six outer petals 82 and six inner petals 82. Other combinations on the outer petals and the inner petals can be practiced without departing from the spirit of the present invention. The plurality of petals 82 then expand outward against the vaginal wall 22 and the cervix 24 (also referred to as being in the second position or the expanded state of the expandable brush 14). The individual or the medical worker keeps the plurality of petals in the female genitalia 20 for a predetermined amount of time, for example, two hours or an amount of time corresponding to overnight. Sleep overnight provides sufficient time for the petals 82 that have been expanded to collect one or more specimens (or multiple specimens) from the interior of the vaginal wall 22 and around the cervix 24, and the plurality of petals 82 and the plurality of bristles 84 collect one or more specimens (or multiple specimens) from the interior of the vaginal wall 22 and around the cervix 24. To phrase it another way, the entirety of the plurality of petals 82 and the plurality of bristles 84 collect a random sampling of specimens in aggregation from the interior of the vaginal wall 22 and around the cervix 24. In one embodiment, the plurality of petals 82 and/or the plurality of bristles 24 actively and passively collects the specimens. As a first example, the plurality of petals 82 and/or the plurality of bristles 24 actively collects specimens through removal or extraction and collection of the specimens after the removal or extraction through direct contact with tissues of the female genitalia 20 or the anal orifice (e.g., the anus and/or the rectum 72) as the self-collecting insertion/delivery plunger device 80 moves or shifts inside the female genitalia 20 or the anal orifice as the individual or patient moves their body, as the female genitalia 20 or the anal orifice moves (e.g., contraction or shifting of the vaginal wall 22, the cervix 24, the anus 70, and/or the rectum 72), as the plurality of petals 82 and/or the plurality of bristles 24 expands inside the female genitalia 20 or the anal orifice and/or the like (e.g., the petals of the plurality petals 82 that directly contacts the vaginal wall 22, the cervix 24, the anus 70, and/or the rectum 72 extracts and collects the specimens). As a second example, the plurality of petals 82 and/or the plurality of bristles 24 passively collects the specimens as they naturally detach from female genitalia 20 (e.g., collects the specimens as they naturally detach or shed from the vaginal wall 22 and/or the cervix 24 and fall onto the plurality of petals 82 and/or the plurality of bristles 24).

Advantageously, the design of the self-collecting insertion/delivery plunger device 80 with the plurality of petals 82 and the plurality of bristles 84 allows a wide capture of specimens. The design of the self-collecting insertion/delivery plunger device 80, from an extraction standpoint, minimizes loss of material. The self-collecting insertion/delivery plunger device 80 further do not get an oversampling of external material compared to internal material because when the self-collecting insertion/delivery plunger device 80 is actually deployed inside of the vagina when inserted a female genitalia.

After the predetermined amount of time has been met, the medical worker (or the patient herself, or the individual herself) removes the self-collecting insertion/delivery plunger device 80 from the female genitalia 20 of the patient (or individual). The self-collected specimens (or specimens collected by a medical worker) are placed in a container for sending to a laboratory for application of the specimens for testing of various symptoms, including sexually transmitted disease (STDs), endometrial cancer screening/uterus cancer screening, cervical cancer screening, or vaginal cancer screening, or any combination of multiple tests.

Figure 13:
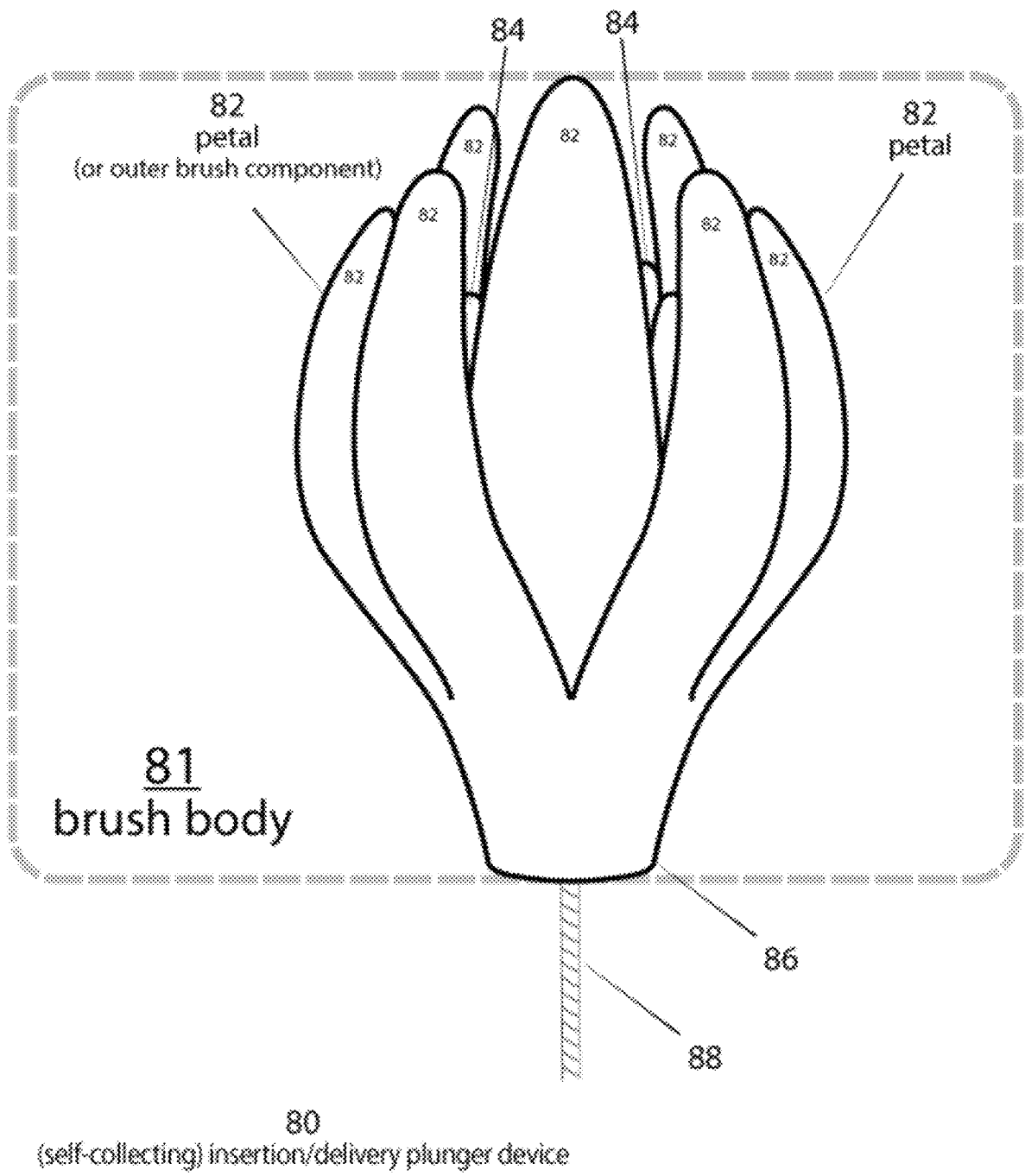
FIG. 13 is a self-collecting insertion/delivery plunger device in a folded form on after collection and when withdrawing (and while keeping one or more samples from being pulled off) in accordance with the present invention.

FIG. 13 is a self-collecting insertion/delivery plunger device 80 in a folded form after collection and when withdrawing (and while keeping one or more samples from being pulled off). As a user pulls out the self-collecting insertion/delivery plunger device 80 from a vagina, the outside surface of the plurality of the petals 82 may wipe off some amount of the specimens, while the plurality of the petals 82 moves toward an enclosure position, as shown in FIG. 13, in capturing and keeping the upper vagina and cervical and uterine cells from getting pulled out or contaminated with other material(s). The enclosure posture of the various petals in the plurality of the petals 82 therefore preserves the collected specimens from the upper vagina and cervical and uterine cells that are within the interior surfaces of the of the plurality of the petals 82 and the plurality of bristles 84, while the exterior surfaces of the various petals in the of the plurality of the petals 82 may have some of the specimens wipe off.

Figure 14:
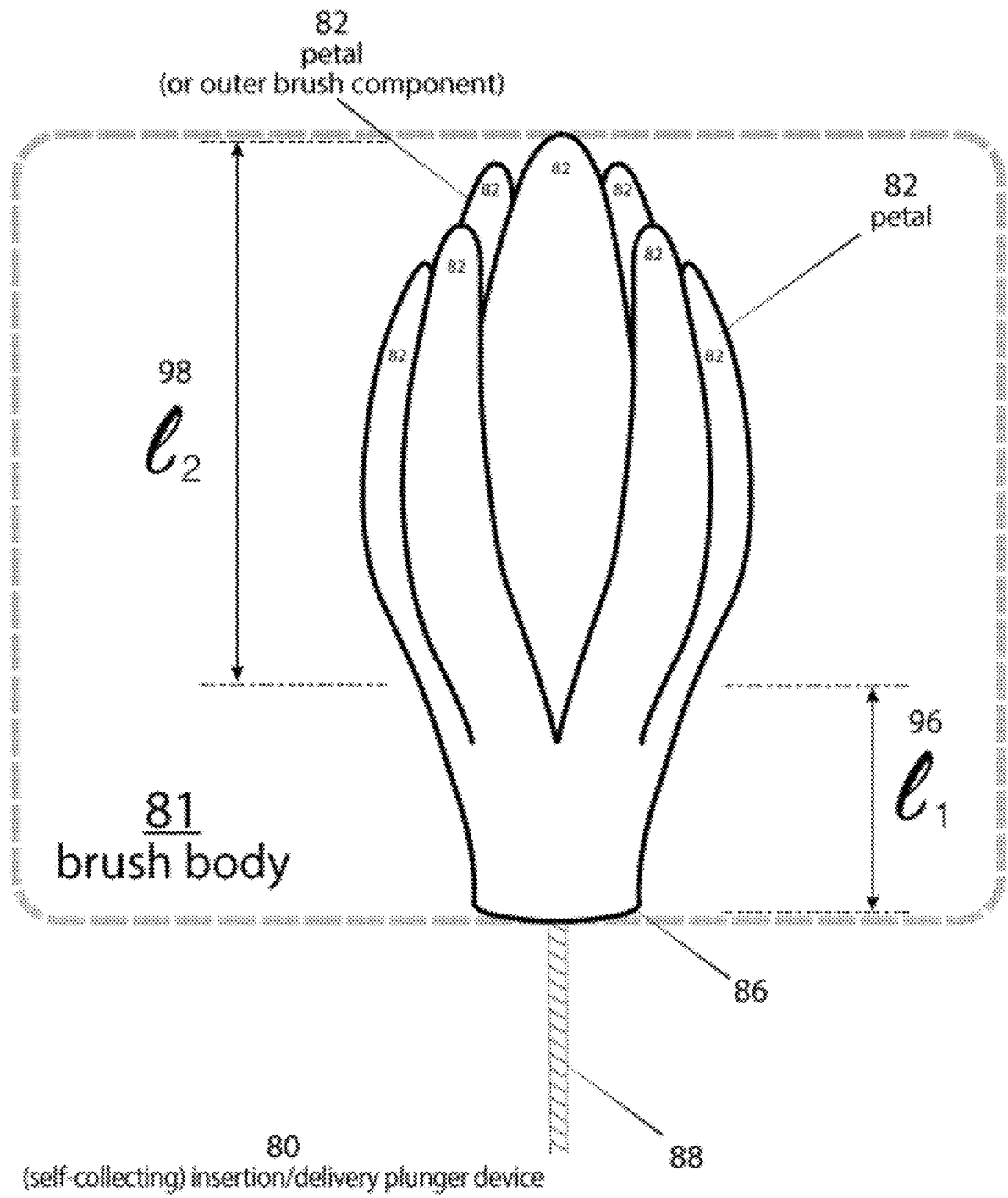
FIG. 14 is a diagram illustrating one example on the length of the base of the self-collecting insertion/delivery plunger device relative to the length in the plurality of the petals in accordance with the present invention.

As an example, the self-collecting insertion/delivery plunger device 80 has the following specification dimensions for manufacturing. In one embodiment, the base 86 of the self-collecting insertion/delivery plunger device 80 is substantially the same length $l_1$ 96 or the same length as the pedal length $l_2$ 98 in the plurality of petals 82, as shown in FIG. 14.

Figure 15:
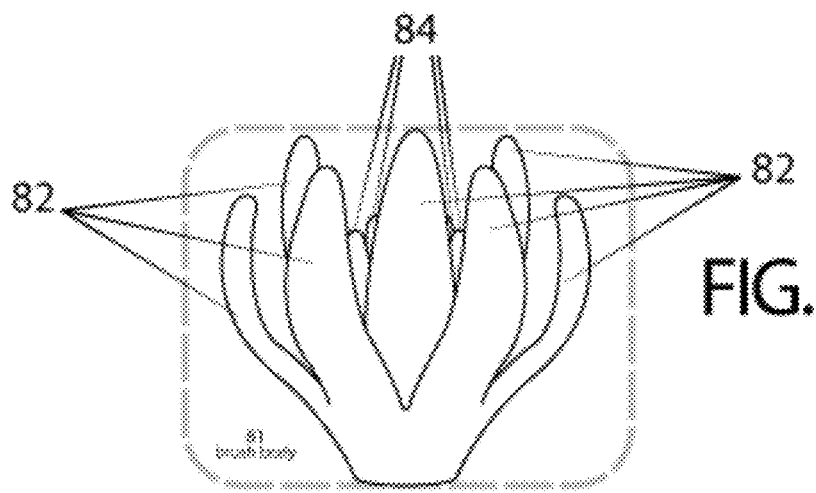
FIG. 15 is a diagram illustrating a first component of a sample implementation with a single piece (or a single unit) of the brush body having the base, the plurality of petal and the plurality of bristles in accordance with the present invention.

FIG. 15 is a diagram illustrating a first component of a sample implementation with a single piece (or "a single unit", or "a single manufactured unit") brush body 81, with a base 83, the plurality of petals 82 and the plurality of bristles 84. In one embodiment, the manufacturing of the brush body 81 having the base 83, the plurality of petals 82 and the plurality of bristles 84 is manufactured as a single unit. One suitable material for the design and manufacturing of the brush body is using medical-grade silicone. The plurality of petals 82 and the plurality of bristles 84 made with the medical-grade silicone have some degree of rigidity, not floppy, to maintain its shapes but also able to expand the petals outward after insertion into a female genitalia.

Figure 16:
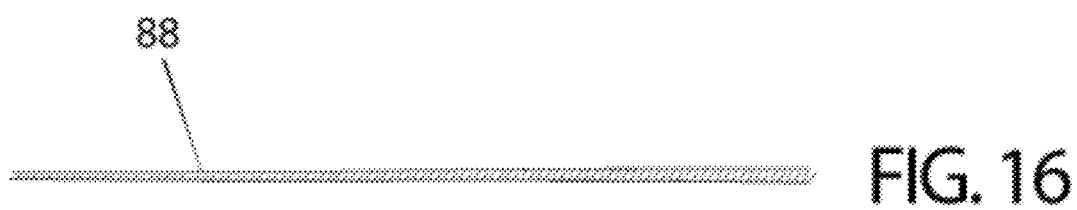
FIG. 16 is a diagram illustrating a second component of the sample implementation with a string in accordance with the present invention.

FIG. 16 is a diagram illustrating a second component of the sample implementation with a string 88. In one embodiment, the string 88 can be designed as a separate component that is attached to the brush body 81. In another embodiment, the forming of the brush body 81 and the string 88 are made out of the same material. The brush body 81 and the string 88 are manufactured as a single unit with the same material. In some embodiments, the string 88 can be selected as having the same or similar strength as medical silicone rubber or another functionally equivalent or similar material.

Figure 17:
FIG. 17 is a diagram illustrating a third component of the sample implementation with an inner tubing having a hollow midsection in accordance with the present invention.

FIG. 17 is a diagram illustrating a third component of the sample implementation with an inner tubing 90 having a hollow midsection 91. The size of the hollow midsection 91 in the inner tubing 90 is suitable for inserting the string 88 through the hollow midsection.

Figure 18:
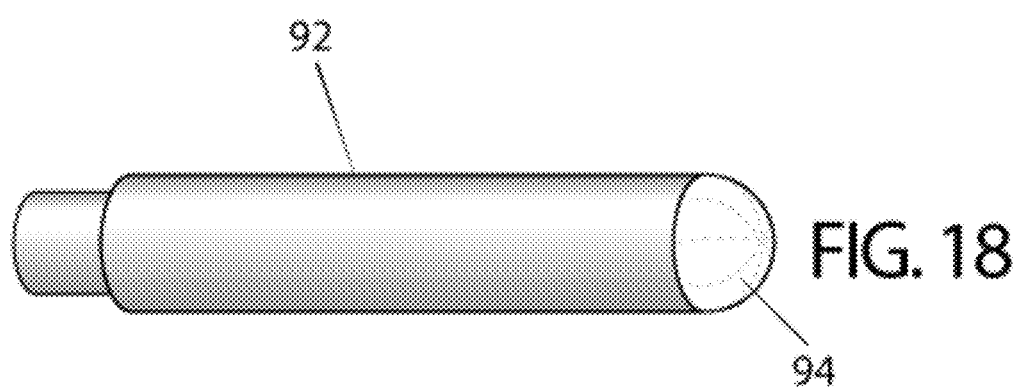
FIG. 18 is a diagram illustrating a fourth component of the sample implementation having an outer tubing with an head that is in a closed position with a plurality petals enclosed when the plurality of petals, the plurality of bristles and the base are inside the outer tubing, and the head is in an open position with the plurality of petals expanded when the plurality of petals, and the plurality of bristles are pressed though the head of the outer tubing in accordance with the present invention.

FIG. 18 is a diagram illustrating a fourth component of the sample implementation with an outer tubing 92 with a head having a plurality petals that can either be in an closed position (also referred to as in the "enclosed position) or an open position. The plurality of petals in the head of the outer tubing 92 is in the enclosed position when the plurality of the petals 82 and the plurality of the bristles 84 are inside the outer tubing 92. The plurality of petals 82 in the head of the outer tubing 92 are in the open position when the plurality of the petals 82 and the plurality of the bristles 84 extended out through a head 94 in the outer tubing 92.

As described above, the self-collecting insertion/delivery plunger device 80 has four components. The first component is the brush body 81 made of medical-grade silicone as single piece 81 that includes the plurality of petals 82, the plurality of bristles 84, and the base 86. The second component is the string 88 that is tied to the medical-grade silicone piece 81. The third component is a thin cylindrical inner tube 90 with hollow center portion. The string 88 can be inserted through the hollow center portion of the thin cylindrical inner tube 90, with a first end of the tube 90 having the string 88, and a second end of the tube 90 having the medical-grade silicone brush body 81. The fourth component is the outer tube 92 which the thin cylindrical inner tube 90 can be inserted.

Figure 19:
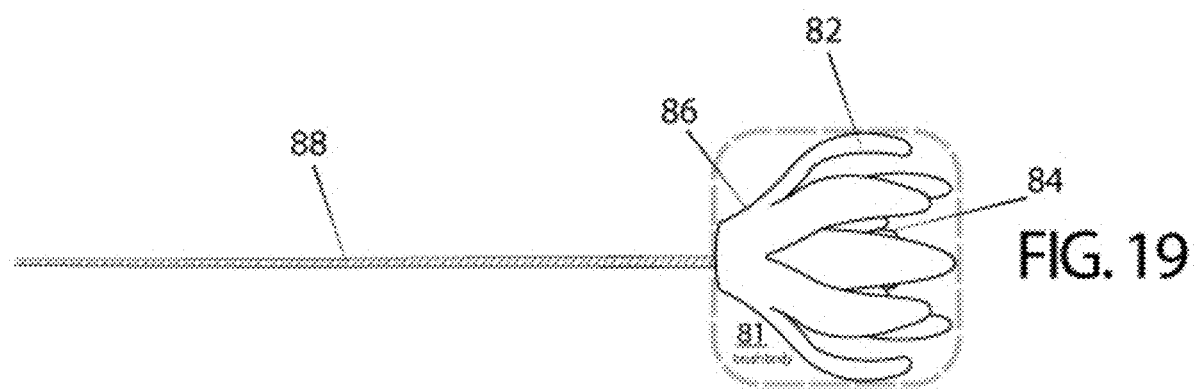
FIG. 19 is a diagram illustrating the second component with the string is attached to the first component with the brush body having the base, the plurality of petals and the plurality of bristles in the implementation in accordance with the present invention.

FIG. 19 is a diagram illustrating one embodiment in which the string 88 is attached to the single piece brush body 81 having the base 86, the plurality of petals 82 and the plurality of bristles 84 in the sample implementation. The string 88 has a length that is longer than the length of the inner tubing 90.

Figure 20:
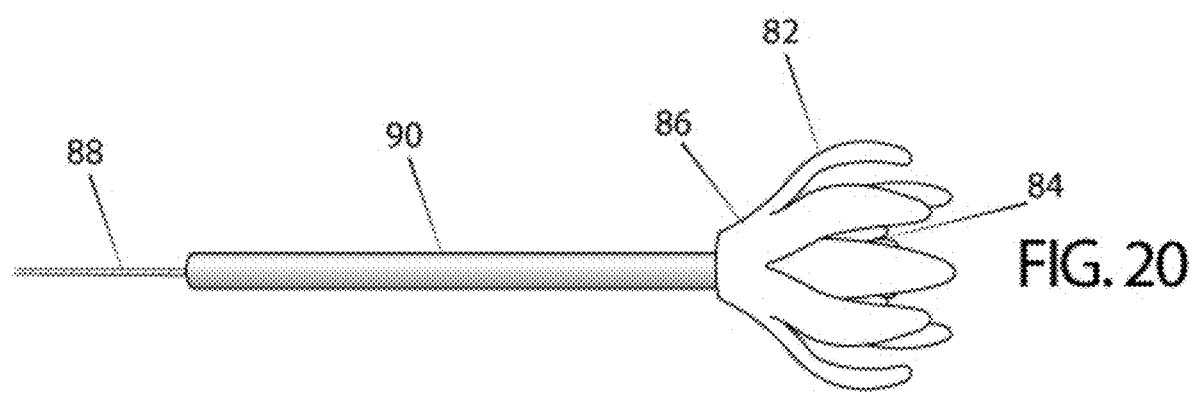
FIG. 20 is a diagram illustrating the string inserted through a hollow midsection of the inner tube, the brush body having the base, the plurality of petals and the plurality of bristles on the one end and the string extending through on the other end in the sample implementation in accordance with the present invention.

FIG. 20 is a diagram illustrating the string 88 having a first end attached to the brush body 81 and a second end. The second end of the string 88 is inserted through hollow midsection 91 of the inner tube 90. As shown in FIG. 20, the brush body 81 extends through one end of the inner tubing 90, while the string extends through the another end of the inner tubing 90.

Figure 21:
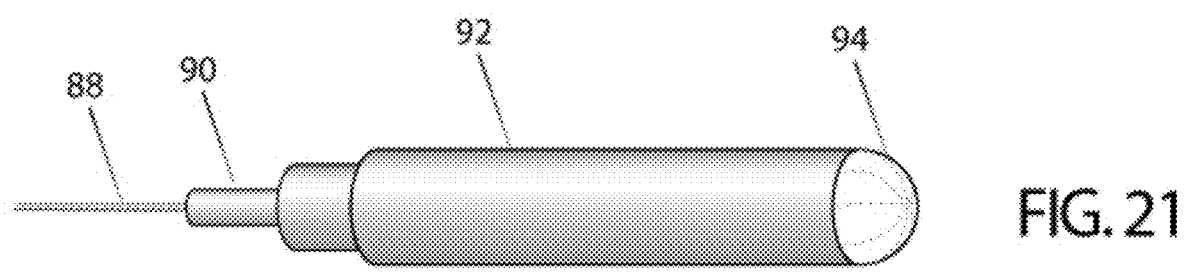
FIG. 21 is a diagram illustrating the placement of the construction in FIG. 21 (with the brush having the base, the plurality of petal and the plurality of bristles, plus the inner tubing, and the string) into the outer tube in the sample implementation in accordance with the present invention.

FIG. 21 is a diagram illustrating the placement of the construction in FIG. 20 (with the brush body 81, the inner tubing 90 and the string 88) into the outer tube 92 with an enclosed head 94 in the sample implementation. The configuration in FIG. 20 with the brush body 81, the inner tubing 90 and the string 88 is inserted into outer tubing 92. On the one end of the outer tubing 92 with the head 94, the brush body 81 remains compressed and inside the head 94. The string 88 and the inner tubing 90 extend out from the other end of the outer tubing 92.

Figure 22:
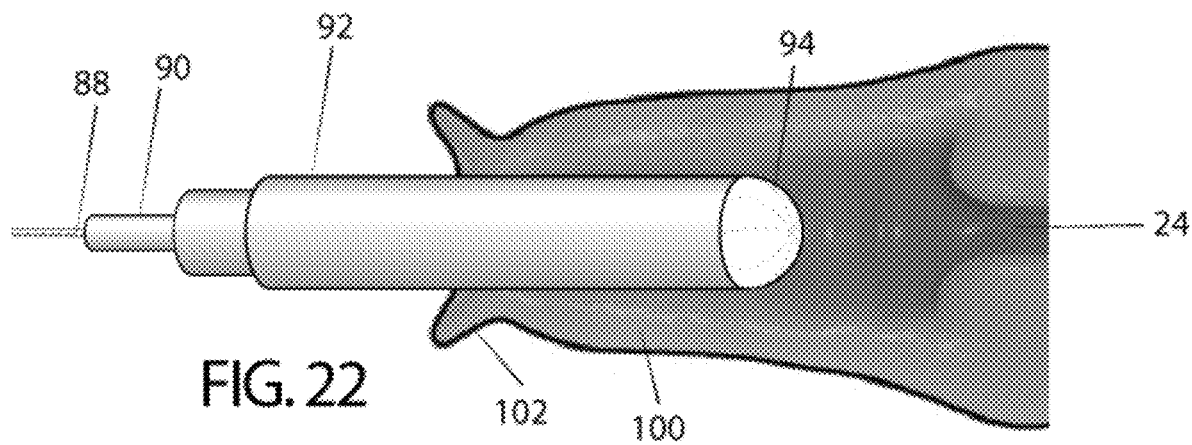
FIG. 22 is a diagram illustrating a first step before the insertion of the self-collecting insertion/delivery plunger device into a vagina when the head of the self-collecting insertion/delivery plunger device is enclosed in the sample implementation in accordance with the present invention.

FIG. 22 is a diagram illustrating a first step before the insertion of the self-collecting insertion/delivery plunger device into a vagina 100 when the head 94 of the self-collecting insertion/delivery plunger device 80 is enclosed in the sample implementation. A person or a medical personnel presses the self-collecting insertion/delivery plunger device 80 into the vagina 100, wherein the head 94 on the outer tubing 92 remains enclosed initially.

Figure 23:
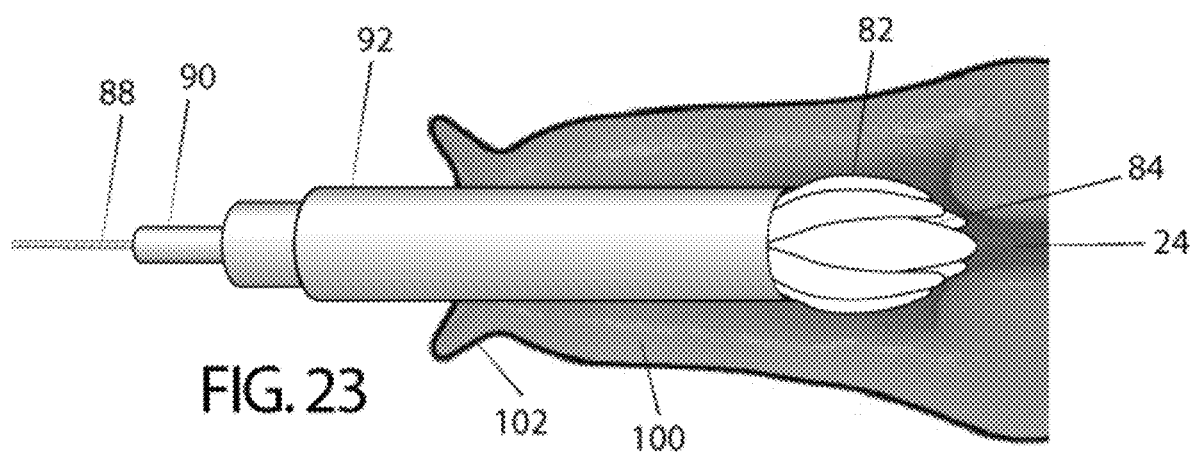
FIG. 23 is a diagram illustrating a second step after the insertion of the self-collecting insertion/delivery plunger device into a vagina when the head of the self-collecting insertion/delivery plunger device opens which the plurality of petals expands through the head of the outer tubing and toward the cervix in the sample implementation in accordance with the present invention.

FIG. 23 is a diagram illustrating a second step after the insertion of the self-collecting insertion/delivery plunger device 80 into an introitus 102 of the vagina 100 when the head 94 opens with the brush body 81 extending through the head 94 toward the cervix 24. The plurality of petals 82 on the brush body 81 remain relative to the compressed form but start to expand.

Figure 24:
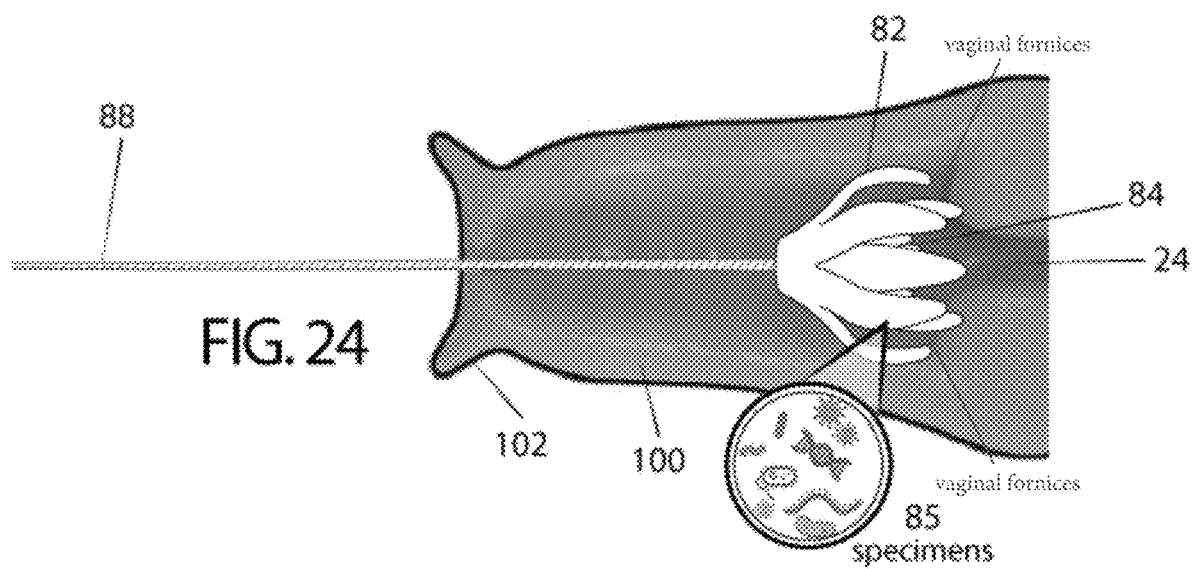
FIG. 24 is a diagram illustrating a third step for removing the outer tubing and the inner tubing from the vagina, while leaving in the brush body having the base, the plurality of petals and the plurality of bristles in the vagina and toward the cervix, with the string extended outside the vagina, in the sample implementation in accordance with the present invention.

FIG. 24 is a diagram illustrating a third step for removing the outer tubing 92 and the inner tubing 90 from the vagina 100, while leaving in the brush body 81 with the plurality of petals 82 expanded and the plurality of bristles 92 expanded around or in the cervix 24. The brush body 81 is attached to the string 88 which extends outside of the vagina 100. In a first example, the positioning of the brush body with the plurality of petals 82 and the plurality of bristles 84 may self-locate itself in the vagina 100, with the plurality of bristles 84 positioned around the midsection of the cervix 24. With the plurality of bristles 84, as well as the plurality of petals 82, positioned around the midsection of the cervix 24, the brush body 81 is able to collect a significant average of specimens 25 from the vagina 100, as viewed from a cellular standpoint and a microbiology standpoint. However, as a second example, with the design of multiple petals in the plurality of petals 82 and the multiple bristles in the plurality of bristles 84, the brush body 81 should also be able to collect a sufficient average of specimens 25 from the vagina 100, even though the brush body 81 is inserted randomly into the vagina 100, which the brush body 81 may tilt toward the right side of the cervix 24, or may tilt toward the left side of the cervix 24, or if the cervix 24 is in a posterior position tilts toward the back or an anterior cervix tilts toward the front. In one embodiment, the sufficient average may correspond to the sufficient average as described in association with FIG. 11, as well as throughout this disclosure.

FIG. 25 is a pictorial diagram illustrating a partial female anatomy 98 comprising the vagina 100, the introitus 102, an external os 104, the cervix 24, a perimetrium 106, an internal os 108, a myometrium 110, an endometrium 112, a uterus 114, a fundus of uterus 118, and a fallopian tube 116. The female anatomy 82 shows that the plurality of petals 82 and the plurality of bristles 84 in the brush body 81 are collecting a plurality of specimens 25, including not limited to bacteria, a virus, DNA, RNA, cervical cells, endometrial cells, vaginal cells, and other applicable cells.

Figure 26:
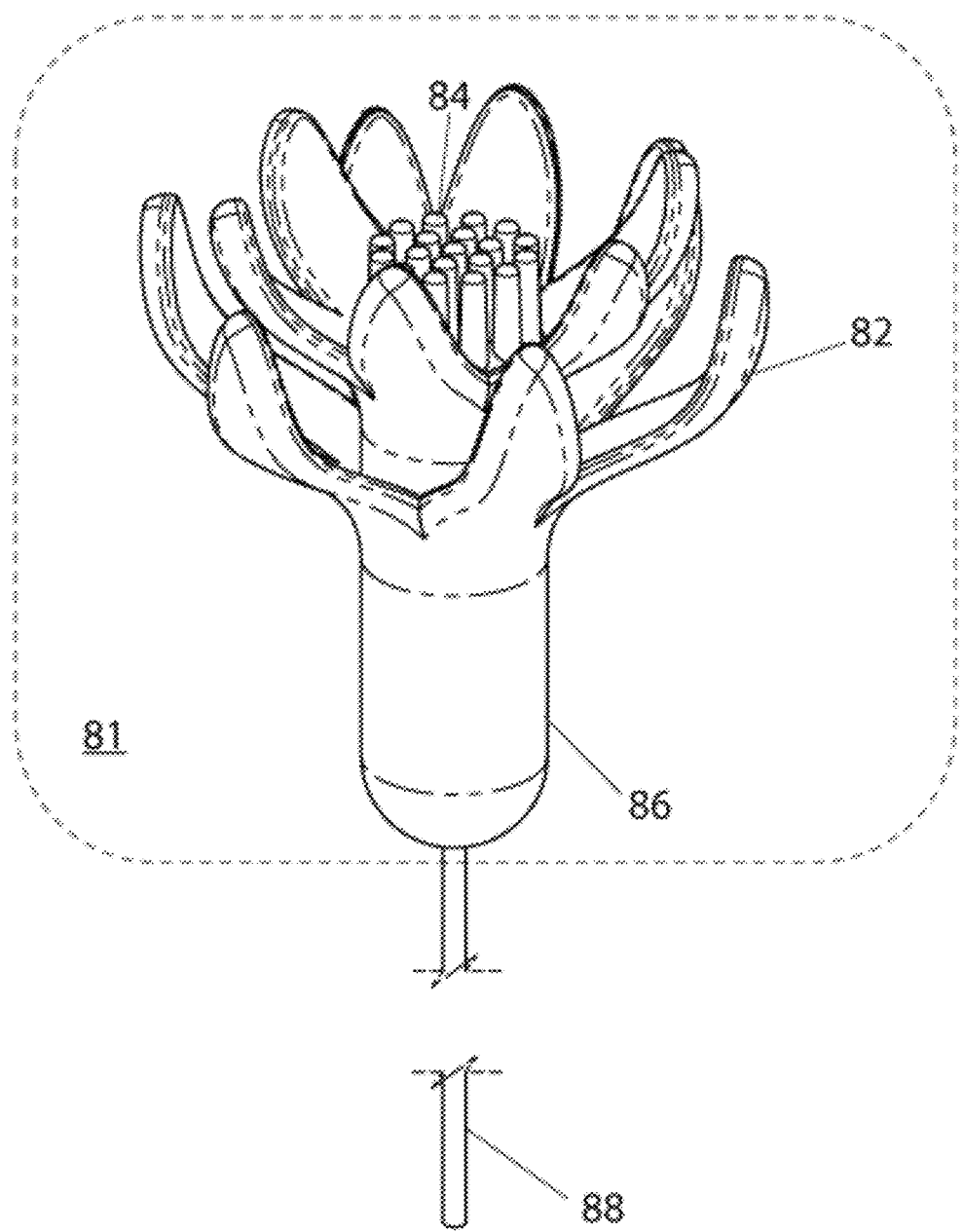
FIG. 26 is a diagram illustrating a perspective view of an example in a manufacturing specification of the brush body and the string in accordance with the present invention.

FIG. 26 is a diagram illustrating a perspective view of an example in a manufacturing specification of the brush body 81 and the string 88 in accordance with the present invention. In this embodiment, the single unit brush body 81 includes six outer petals 82*a*, six inner petals 82*b*, and the plurality of bristles 84. The collective of the six outer petals 82*a*, six inner petals 82*b* is referred to generally in the specification as the plurality of petals 82.

Figure 27:
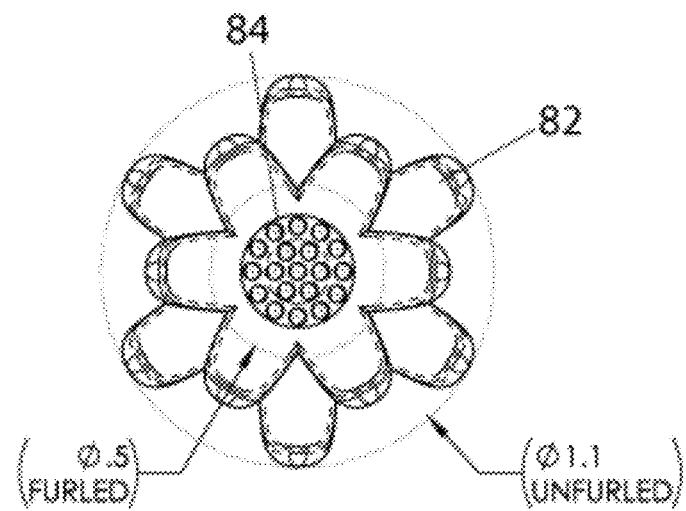
FIG. 27 is a diagram illustrating a top view of the example in the manufacturing specification with respect to FIG. 26 of the brush body and the string in accordance with the present invention.

FIG. 27 is a diagram illustrating a top view of the example in the manufacturing specification with respect to FIG. 26 of the brush body 81 and the string 88. From the top view of the brush body 81, the plurality of bristles 84 are shown in the center of the brush body 81. Just to reiterate, one of skill in the art would recognize that the actual of number of bristles is selected depending on the design. The six inner petals 82*b* (in the plurality of petals 82) are shown surrounding the plurality of bristles 84. The six inner petals 82*b* (in the plurality of petals 82) are shown surrounding by the six outer petals 82*a*.

Figure 28:
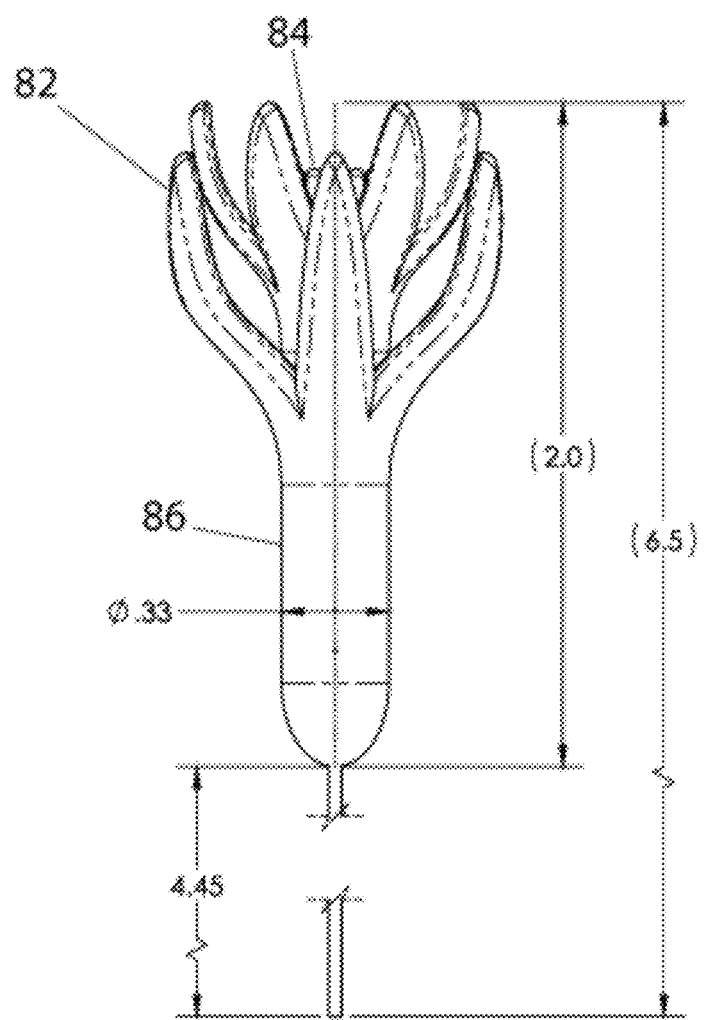
FIG. 28 is a diagram illustrating a perspective view of the example in the manufacturing specification with respect to FIG. 26 of the plurality of petals in the brush body and the string in accordance with the present invention.

FIG. 28 is a diagram illustrating a perspective view of the example in the manufacturing specification with respect to FIG. 26 of the plurality of petals in the brush body 81 and the string 88. Sample measurements on the respective length of the petals 82, the based 86, and the string 88 are shown in FIG. 28.

Figure 29:
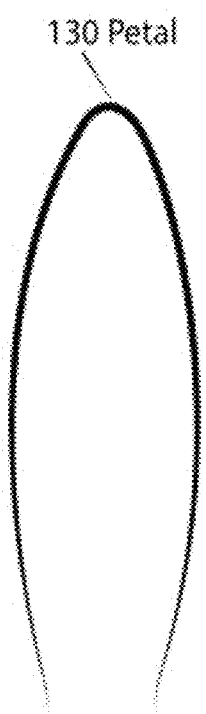
FIG. 29 is a diagram illustrating one embodiment in the enlargement of one petal shape in accordance with the present invention.
Figure 30:
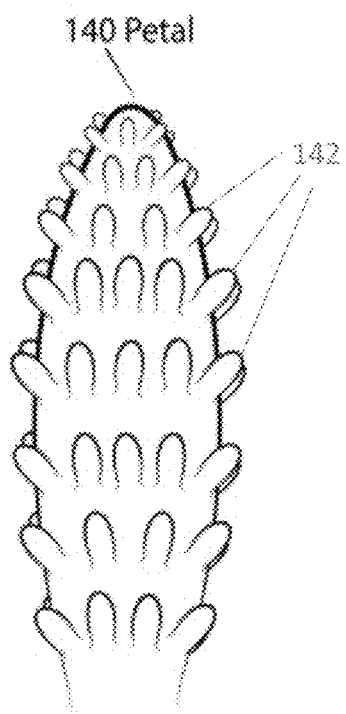
FIG. 30 is a diagram illustrating another embodiment in the enlargement of another petal shape in accordance with the present invention.
Figure 31:
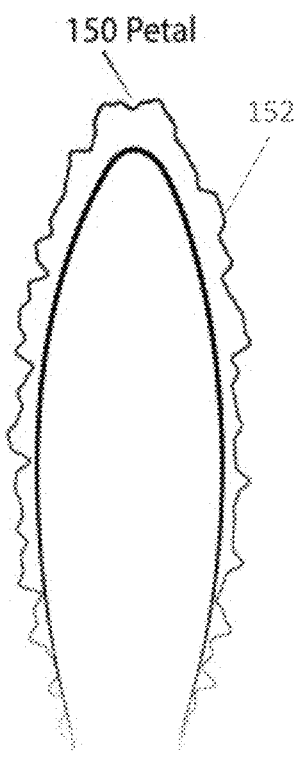
FIG. 31 is a diagram illustrating a further embodiment in the enlargement of a further petal shape in accordance with the present invention.

FIG. 29 is a diagram illustrating one embodiment in the enlargement of a petal 130. The petal 130 is designed in an oval shape (or an ellipse shape). FIG. 30 is a diagram illustrating another embodiment in the enlargement of a petal 140. The petal 140 is a petal having a plurality of spaced-apart protruding mini-petals 142. FIG. 31 is a diagram illustrating a further embodiment in the enlargement of a petal 150. The petal 150 is a petal having a serrated edge 152. Each of the petal 130, the petal 140, or the petal 150 is designed in an oval shape (or an ellipse shape) and can be used to implement any of the embodiments described above in the present invention. Medical-grade silicone rubber or another functionally equivalent or similar material may be used to manufacture petal 130, petal 140, or petal 150. In one embodiment, at least the mini-petals 142 and/or the serrated edge 152 extracts or removes the specimens as the mini-petals 142 and/or the serrated edge 152 directly contacts and/or moves while contacting a wall or portion of the female genitalia 20 or the anal orifice (e.g., as the petals 140 and 150 directly contacts and/or moves while contacting the vaginal wall 22, the cervix 24, the anus 70, and/or the rectum 72).

Figure 32:
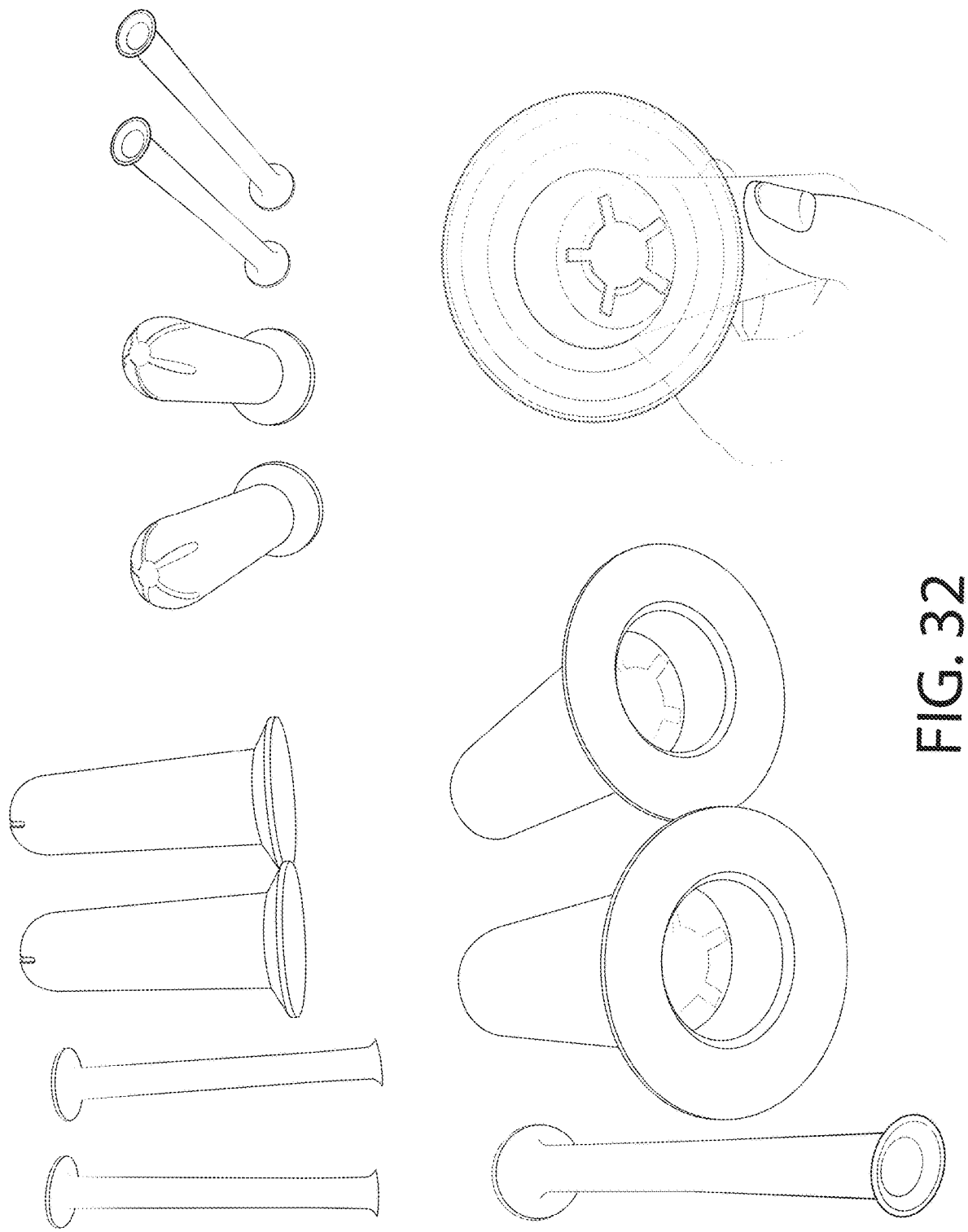
FIG. 32 is a diagram illustrating an example of the outer tubular member and the inner tubular member, without the brush body, of the insertion plunger device in accordance with the present invention.

FIG. 32 shows a diagram illustrating an example of the outer tubular member and the inner tubular member, without the brush body, of the insertion plunger device in accordance with the present invention.

Figure 33:
FIG. 33 is a diagram illustrating a trademark logo of VagiGuard™.
Figure 34:
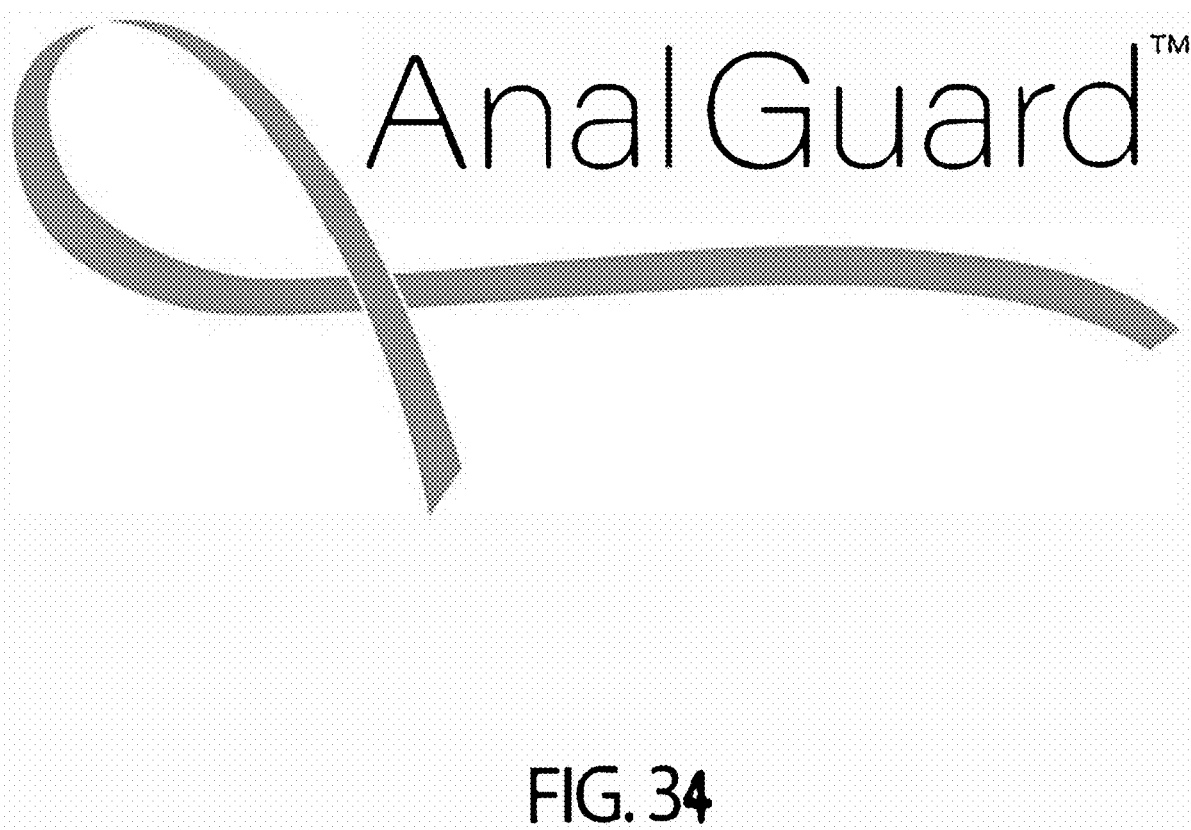
FIG. 34 is a diagram illustrating a trademark logo of AnalGuard™.

FIG. 33 is a diagram illustrating a trademark logo of VagiGuard™, which has a ribbon symbol as shown placed underneath the text. FIG. 34 is a diagram illustrating a trademark logo of AnalGuard™, which has a ribbon symbol as shown placed underneath the text.

In one embodiment, a specimen collection device comprises a generally cylindrical tubing casing; and a brush body placed into the tubing casing, the brush body comprising a plurality of bristles on a first end and a string attached on a second end; wherein the specimen collection device functions between a first state and a second state, the plurality of bristles on the brush body remaining in an unexpanded form during the first state, the plurality of bristles on the brush body expanding outward in an expanded form during the second state, and, during the second state, the plurality of bristles collects specimens from an orifice of a patient when inserted into the orifice for a predetermined amount of time.

In another embodiment, a specimen collection device comprises an outer tubular member; and an inner tubular member inserted through the outer tubular member; a single-unit brush body comprising a plurality of petals and a plurality of bristles, the single-unit brush body attached to a string, the string of the brush body inserted through the inner tubular member; wherein the specimen collection device functions between a first state and a second state, the plurality of petals and the plurality of bristles on the brush body remaining in an unexpanded form during the first state, the plurality of petals and the plurality of bristles on the brush body expanding outward in an expanded form during the second state, and during the second state, the plurality of petals and the plurality of bristles collect a plurality of specimens from an orifice of a patient when inserted into the orifice for a predetermined amount of time.

In a further embodiment, a specimen self-collection device comprises an outer tubular member; and an inner tubular member inserted through the outer tubular member; a brush body with a string, the string of the brush body inserted through the inner tubular member, the brush body comprising a plurality of specimen collection elements; wherein the specimen self-collection device functions in a first state and a second state, the plurality of specimen collection elements on the brush body remaining in an unexpanded form during the first state, the plurality of specimen collection elements on the brush body expanding outward in an expanded form during the second state, and, during the second state, the plurality of specimen collection elements collects specimens when inserted into an orifice for a predetermined amount of time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to "an inclusive or" and "not to an exclusive or". For example, a condition A or B is satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention described herein can be implemented in numerous ways, including as a computational method of process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to one possible embodiment. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. In addition, the particular division of functionality between the various system components described herein is merely exemplary, and not mandatory; functions performed by a single system component may instead be performed by multiple components, and functions performed by multiple components may instead be performed by a single component.

An ordinary artisan should require no additional explanation in developing the methods and systems described herein but may find some possibly helpful guidance in the preparation of these methods and systems by examining standard reference works in the relevant art.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the invention claimed herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present invention, without departing from the spirit and scope of embodiments defined in the following claims, the scope of which is to be accorded the broadest interpretation so as to encompass such modifications and equivalent structures.

What is claimed is:

1. A specimen collection device, comprising:
a generally cylindrical tubing casing;
and a brush body constructed as a single material piece for insertion into the tubing casing,
the brush body comprising a plurality of bristles on a first end and a string attached on a second end,
the brush body comprising a medical-grade silicone material with a tensile strength that matches with an anatomical parameter of a vaginal orifice,
the medical-grade silicone material used in the plurality of bristles possessing the tensile strength to withstand a compressive force of at least one muscle of the vaginal orifice;
wherein the specimen collection device transitions between an unexpanded state and an expanded state,
the plurality of bristles on the brush body remaining in an unexpanded state,
the plurality of bristles on the brush body are configured to expand outward inside the vaginal orifice during the expanded state,
the plurality of bristles, in the expanded state, are configured to be directly in contact with a vaginal wall and cervix in the vaginal orifice,
the plurality of bristles on the brush body have a tensile strength that matches with an anatomical parameter of the vaginal orifice,
the plurality of bristles self-locate by adjusting at least one position and/or at least one orientation towards a wider section inside the vaginal orifice,
and during the expanded state, the plurality of bristles are configured to collect specimens from the vaginal orifice of a patient when inserted into the vaginal orifice for a predetermined amount of time,
the plurality of bristles having an elasticity to transition between the expanded state and the unexpanded state;
wherein the brush body further comprises a plurality of petals surrounding the plurality of bristles,
wherein the plurality of petals are constructed with an outer layer having a plurality of outer petals and an inner layer having a plurality of inner petals,
wherein the outer layer concentrically surrounds the inner layer such that the inner petals are located between openings of the outer petals.

2. The device of claim 1,
wherein the anatomical parameter comprises a vaginal tone.

3. The device of claim 1,
wherein the plurality of bristles collect the specimens from a surface of the vaginal orifice.

4. The device of claim 1,
wherein the specimen collection device is configured to transition from the first state to the second state when the brush body exits the tubing casing.

5. The device of claim 1,
wherein the specimen collection device is configured to transition from the second state to the first state while the brush body is being withdrawn from the vaginal orifice.

6. The specimen collection device of claim 1,
wherein the plurality of bristles comprise a tensile portion at an amount that withstands a compressive force at least one muscle of an anus such that the compressive force does not cause the plurality of bristles to disassemble and the compressive force does not harm the vaginal orifice.

7. The specimen collection device of claim 1,
further comprising a plurality of petals,
the plurality of petals folding over the plurality of bristles to reduce the loss of specimens during removal when specimen collection device transitions from the expanded state to the unexpanded state.

8. A specimen collection device, comprising:
an outer tubular member;
and an inner tubular member inserted through the outer tubular member;
a single-unit brush body having a single material and comprising a brush portion,
the brush portion having a plurality of foldable petals and a plurality of bristles,
the single-unit brush body attached to a string,
the string of the brush body inserted through the inner tubular member,
the single- unit brush body comprising a medical-grade silicone material that possesses a tensile strength to withstand a compressive force of at least one muscle and tone of a vaginal orifice;
wherein the specimen collection device transitions between an unexpanded state in a folded form and an expanded state,
the plurality of foldable petals and the plurality of bristles on the brush body remaining in an unexpanded form during the unexpanded state,
the plurality of foldable petals and the plurality of bristles expand outward in an expanded form inside the vaginal orifice during the expanded state,
the plurality of foldable petals and the plurality of bristles, in the expanded state, are configured to directly contact a vaginal wall and cervix in the vaginal orifice,
the plurality of foldable petals having a thickness,
a tensile strength,
and an elasticity sufficient to transition between the expanded state and the unexpanded state,
the plurality of foldable petals having a tensile strength that matches with an anatomical parameter of the vaginal orifice,
the plurality of foldable petals self-locate when inserted into a vaginal orifice toward a cervix to collect specimens,
and during the expanded state,
the plurality of foldable petals and the plurality of bristles collect a plurality of specimens from the vaginal orifice of a patient when inserted into the vaginal orifice for a predetermined amount of time;

and in the expanded state,
the brush body and the plurality of foldable petals possess sufficient thickness, tensile strength, and elasticity to facilitate the expansion and to self locate the plurality of foldable petals adjacent to the cervix and within vaginal fornices;
wherein the brush body further comprises a plurality of petals surrounding the plurality of bristles,
wherein the plurality of petals are constructed with an outer layer having a plurality of outer petals and an inner layer having a plurality of inner petals,
wherein the outer layer concentrically surrounds the inner layer such that the inner petals are located between openings of the outer petals.

9. The specimen collection device of claim 8,
wherein each petal comprises a plurality of spaced-apart protruding mini-petals,
the elasticity of plurality of the mini-petals facilitating expansion of the mini-petals in the expanded state.

10. The specimen collection device of claim 8,
wherein each petal has a serrated edge adapted to extract the specimens as the serrated edge directly contacts a vaginal wall of the vaginal orifice.

11. The specimen collection device of claim 8,
wherein the plurality of petals and the plurality of bristles on transitions from the expanded state to the unexpanded state when being withdrawn from the vaginal orifice.

12. The specimen collection device of claim 11,
wherein the plurality of petals surrounds the plurality of bristles such that during the first state,
the plurality of petals closes around the plurality of bristles and preserves the plurality of specimens within the brush body.

13. The specimen collection device of claim 8,
wherein the plurality of petals and the plurality of bristles on transitions from the unexpanded state to the expanded state when the brush body exits the outer tubular member.

14. The specimen collection device of claim 8,
wherein the plurality of petals comprises twelve petals, constructed with six outer petals and six inner petals.

15. The specimen collection device of claim 8,
wherein the plurality of petals on the brush body adjusts to a position adjacent to a cervix in a female genitalia to collect the plurality of specimens.

16. The specimen collection device of claim 8,
wherein the anatomical parameter comprises a vaginal tone.

17. The specimen collection device of claim 8,
wherein the plurality of petals and the plurality of bristles comprise a medical-grade silicone that maintains a shape of the plurality of petals and a shape of the plurality of bristles during the second state.

18. The specimen collection device of claim 8,
wherein the plurality of outer petals fold over the plurality of inner petals to reduce the loss of specimens during removal when specimen collection device transitions from the expanded state to the unexpanded state.

19. The specimen collection device of claim 8,
wherein the brush portion self-locates by adjusting at least one position and/or at least one orientation of the plurality of petals and the plurality of bristles towards a wider section inside the vaginal orifice.

20. The specimen collection device of claim 8,
wherein the plurality of specimens comprise microbiology samples such that the plurality of petals and the plurality of bristles collect a sufficient amount of the microbiology samples to enable visualization of a condition being tested for on a microscope slide.

21. The specimen collection device of claim 8,
wherein the plurality of specimens comprise molecular samples such that the plurality of petals and the plurality of bristles collect a sufficient amount of the molecular samples to accurately diagnose a condition using molecular analysis.

22. The specimen collection device of claim 8,
wherein the plurality of specimens comprise pathology samples such that the plurality of petals and the plurality of bristles collect a sufficient amount of the pathology samples to perform a cytology analysis.

23. The specimen collection device of claim 8,
wherein the plurality of petals and the plurality of bristles are made of a material that has passed the United States Food and Drug Administration (FDA) biocompatibility testing.

24. A specimen self-collection device, comprising:
an outer tubular member;
and an inner tubular member inserted through the outer tubular member;
and a brush body constructed as a single material piece with a string,
the string of the brush body inserted through the inner tubular member,
the brush body comprising a brush portion,
the brush portion having a plurality of petals and a plurality of bristles,
the plurality of petals constructed with an outer layer having a plurality of outer petals and an inner layer having a plurality of inner petals,
each petal in the plurality of outer petals being wider than every taped petal in the plurality of inner petals,
the brush body comprising a medical-grade silicone material that possesses a tensile strength to withstand a compressive force of at least one muscle and a vaginal tone of a vaginal orifice;
wherein the specimen self-collection device functions in an unexpanded state and an expanded state,
the plurality of petals and the plurality of bristles remaining in the unexpanded state,
the plurality of petals and the plurality of bristles are configured to expand outward into an expanded form inside the vaginal orifice during the second state,
the plurality of petals and the plurality of bristles, in the expanded state, are configured to directly contact a vaginal wall and cervix of a female genitalia,
the plurality of petals having a tensile strength that matches with an anatomical parameter of the vaginal orifice,
the plurality of petals self-locate when inserted into the vaginal orifice toward a cervix in a female genitalia to collect specimens,
and during the expanded state, the plurality of petals and the plurality of bristles are configured to collect specimens when inserted into the female genitalia for a predetermined amount of time,
the plurality of petals having an elasticity to transition between the expanded state and the unexpanded state;
wherein the brush body further comprises a plurality of petals surrounding the plurality of bristles,
wherein the plurality of petals are constructed with an outer layer having a plurality of outer petals and an inner layer having a plurality of inner petals, wherein the outer layer concentrically surrounds the inner layer such that the inner petals are located between openings of the outer petals.

25. The specimen collection device of claim 24, wherein the plurality of outer petals fold over the plurality of inner petals to reduce the loss of specimens during removal when specimen collection device transitions from the expanded state to the unexpanded state.

26. A specimen collection device, comprising:
an outer tubular member;
and an inner tubular member inserted through the outer tubular member;
and a brush body constructed as a single material piece,
the brush body comprising a plurality of petals and a plurality of bristles,
the brush body attached to a string,
the string inserted through the inner tubular member,
wherein the plurality of petals are foldable,
wherein the plurality of petals are constructed with an outer layer having a plurality of outer petals and an inner layer having a plurality of inner petals,
each petal in the plurality of outer petals being wider than every taped petal in the plurality of inner petals,
the brush body comprising a medical-grade silicone material that possesses a tensile strength to withstand a compressive force of at least one muscle and tone of a vaginal orifice;
wherein the specimen collection device transitions between an unexpanded state in a folded form and an expanded state,
the plurality of petals and the plurality of bristles remaining in the folded form during the unexpanded state,
the plurality of petals and the plurality of bristles are configured to expand outward into an expanded form inside a female genitalia during the second state in the expanded state,
the plurality of petals and the plurality of bristles, in the expanded state, are configured to directly contact a vaginal wall and cervix in the female genitalia,
the plurality of petals having a tensile strength that matches with an anatomical parameter of the vaginal orifice,
the plurality of petals on the brush body self-locate when inserted into the vaginal orifice toward a cervix in a female genitalia to collect specimens,
and during the expanded state, the plurality of petals and the plurality of bristles are configured to actively collect a plurality of specimens from female genitalia of a patient when inserted into the female genitalia for a predetermined amount of time,
the plurality of petals and/or the plurality of bristles are further configured to passively collect the specimens that naturally detach or shed from the vaginal wall and/or the cervix of the female genitalia and fall onto the plurality of petals and/or the plurality of bristles,
the plurality of petals having an elasticity configured to transition between the expanded state and the unexpanded state;
wherein the brush body further comprises a plurality of petals surrounding the plurality of bristles,
wherein the plurality of petals are constructed with an outer layer having a plurality of outer petals and an inner layer having a plurality of inner petals,
wherein the outer layer concentrically surrounds the inner layer such that the inner petals are located between openings of the outer petals.

* * * * *